US011257476B2

(12) United States Patent
Hayashi et al.

(10) Patent No.: US 11,257,476 B2
(45) Date of Patent: Feb. 22, 2022

(54) SIGNAL PROCESSING APPARATUS AND SIGNAL PROCESSING METHOD

(71) Applicant: SONY CORPORATION, Tokyo (JP)

(72) Inventors: Shigetoshi Hayashi, Tokyo (JP); Kohei Asada, Kanagawa (JP); Shinpei Tsuchiya, Saitama (JP); Kazunobu Ookuri, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/979,155

(22) PCT Filed: Mar. 8, 2019

(86) PCT No.: PCT/JP2019/009273
§ 371 (c)(1),
(2) Date: Sep. 8, 2020

(87) PCT Pub. No.: WO2019/176757
PCT Pub. Date: Sep. 19, 2019

(65) Prior Publication Data
US 2020/0402494 A1 Dec. 24, 2020

(30) Foreign Application Priority Data
Mar. 16, 2018 (JP) ............................ JP2018-049843

(51) Int. Cl.
*A61F 11/06* (2006.01)
*G10K 11/178* (2006.01)
*G10K 11/16* (2006.01)

(52) U.S. Cl.
CPC .................. *G10K 11/17881* (2018.01); *G10K 2210/3023* (2013.01); *G10K 2210/3026* (2013.01);
(Continued)

(58) Field of Classification Search
CPC ..... G10K 11/17881; G10K 2210/3023; G10K 2210/3026; G10K 2210/3027; G10K 2210/3036; G10K 2210/3046
(Continued)

(56) References Cited

U.S. PATENT DOCUMENTS 5,774,564 A * 6/1998 Eguchi ............ G10K 11/17881 381/71.11
6,522,753 B1 2/2003 Matsuzawa et al.
(Continued)

FOREIGN PATENT DOCUMENTS

CN 102473405 A 5/2012
JP 04-349498 A 12/1992
(Continued)

OTHER PUBLICATIONS

International Search Report and Written Opinion of PCT Application No. PCT/JP2019/009273, dated May 28, 2019, 10 pages of ISRWO.

*Primary Examiner* — Ammar T Hamid
(74) *Attorney, Agent, or Firm* — Chip Law Group

(57) ABSTRACT

Provided is a signal processing apparatus of a plurality of signal processing apparatuses that includes a noise canceling processing unit capable of connecting one or more input portions and one or more output portions, and performs a noise canceling processing. Signal processing apparatuses of the plurality of signal processing apparatuses are connected to one another.

14 Claims, 22 Drawing Sheets

(52) U.S. Cl.
CPC ................ *G10K 2210/3027* (2013.01); *G10K 2210/3036* (2013.01); *G10K 2210/3046* (2013.01)

(58) Field of Classification Search
USPC ................................................ 381/71.1, 71.4
See application file for complete search history.

(56) References Cited

U.S. PATENT DOCUMENTS

| | | | | |
|---|---|---|---|---|
| 2005/0055116 | A1* | 3/2005 | Isaka | G10L 21/0208 700/94 |
| 2011/0007907 | A1* | 1/2011 | Park | G10K 11/17881 381/71.8 |
| 2018/0197527 | A1 | 7/2018 | Guiu et al. | |

FOREIGN PATENT DOCUMENTS

| | | | | |
|---|---|---|---|---|
| JP | 07-110693 | A | | 4/1995 |
| JP | 07-281676 | A | | 10/1995 |
| JP | 09-230874 | A | | 9/1997 |
| JP | 2000-112483 | A | | 4/2000 |
| JP | 2003-216163 | A | | 7/2003 |
| JP | 2009-251533 | A | | 10/2009 |
| JP | 2009251533 | A | * | 10/2009 |
| JP | 2012-533091 | A | | 12/2012 |
| JP | 2015-080199 | A | | 4/2015 |
| KR | 10-2012-0042954 | A | | 5/2012 |
| WO | 2017/017038 | A1 | | 2/2017 |
| WO | 2017/175448 | A1 | | 10/2017 |

* cited by examiner

Sensitivity function $y = \frac{1}{1+\beta_1 H} NF$

Sensitivity function $y = \frac{(1+\beta_2 H')}{1+\beta_2 (H'-H)} NF$

Sensitivity function $y = \frac{(1+\beta_2 H')}{1+\beta_2(H'-H)+H\beta_1} NF$

| Stream type | Bus type | |
|---|---|---|
| Input/output data | Control data | Module data |
| 1 Audio signal<br>2 Cancellation signal<br>3 Transfer function<br>⋮ | Noise canceling on/off<br>⋮ | 1 Arrangement setting information<br>2 Importance information<br>3 Module number<br>⋮ |

SIGNAL PROCESSING APPARATUS AND SIGNAL PROCESSING METHOD

CROSS REFERENCE TO RELATED APPLICATIONS

This application is a U.S. National Phase of International Patent Application No. PCT/JP2019/009273 filed on Mar. 8, 2019, which claims priority benefit of Japanese Patent Application No. JP 2018-049843 filed in the Japan Patent Office on Mar. 16, 2018. Each of the above-referenced applications is hereby incorporated herein by reference in its entirety.

TECHNICAL FIELD

The present technology relates to a signal processing apparatus, a signal processing method, and a signal processing program.

BACKGROUND ART

Conventionally, a technique of noise canceling for noise reduction in space by using a predetermined number of speakers and microphones, is proposed (Patent Document 1).

In addition, in the control of noise in a particular closed space, it is known that the performance of noise reduction is improved by using a system configuration in which mutual interference between multi-inputs and multi-outputs (Multi Input-Multi Output) is considered. This differs from single-input and single-output as seen in headphone noise canceling.

CITATION LIST

Patent Literature

Patent Literature 1: Japanese Patent Application Laid-open No. 2015-080199

DISCLOSURE OF INVENTION

Technical Problem

However, considering the size of the space to be controlled and the resources of signal processing, it is not efficient to implement the configuration of multi-inputs and multi-outputs in a single noise canceling system. At the same time, the configuration of multi-inputs and multi-outputs has a problem that the scale of the system becomes large.

The present technology has been made in view of such problems. It is an object of the present technology to provide a signal processing apparatus capable of easily adjusting the scale of the object range of the noise canceling processing. It is an object of the present technology to provide a signal processing method and a signal processing program.

Solution to Problem

In order to solve the problems described above, according to a first technique, there is provided a noise canceling processing unit connectable to one or a plurality of input units and connectable to one or a plurality of output units, a plurality of the signal processing apparatuses being connected one another and configured to execute noise canceling processing.

Further, according to a second technique, there is provided a signal processing method, including: connecting a plurality of signal processing apparatuses one another and executing noise canceling processing, each of the plurality of signal processing apparatuses including a noise canceling processing unit connectable to one or a plurality of input units and connectable to one or a plurality of output units.

Further, according to a third technique, there is provided a signal processing program that causes a computer to execute a signal processing method including connecting a plurality of signal processing apparatuses one another and executing noise canceling processing, each of the plurality of signal processing apparatuses including a noise canceling processing unit connectable to one or a plurality of input units and connectable to one or a plurality of output units.

Advantageous Effects of Invention

According to the present technology, it is possible to easily adjust the scale of the target range of the noise canceling processing. It should be noted that the effects of the present technology are not limited to the effects described herein. The present technology may have any of the effects described herein.

MODE(S) FOR CARRYING OUT THE INVENTION

Embodiments of the present technology will be described below with reference to the drawings. Note that the description is made in the following order.

<1. Embodiment>

[1-1. Configuration of Signal Processing Unit]

[1-2. Connection of Signal Processing Apparatuses]

[1-3. Data Transfer]

[1-3-1. First Example of a Circular Array]

[1-3-2. Second Example of a Circular Array]

[1-3-3. Direction of data transfer]

[1-3-4. Packing in Data Transfer]

<2. Modifications>

1. Embodiment

[1-1. Configuration of Signal Processing Unit]

Figure 1:
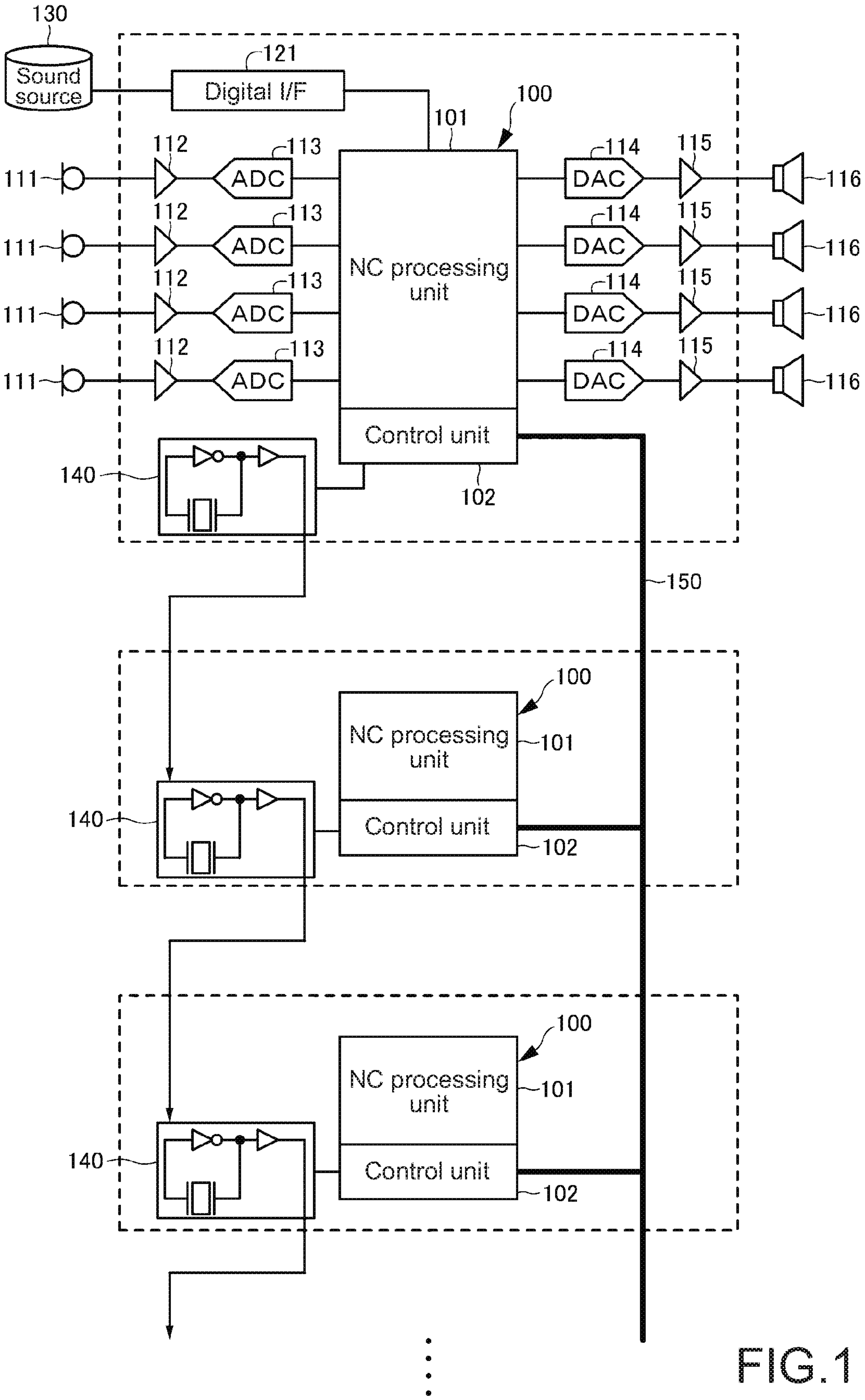
FIG. 1 A block diagram showing a configuration of a signal processing apparatus according to an embodiment of the present technology.

It will be described first the configuration of the signal processing apparatus 100 with reference to FIG. 1. The signal processing apparatus 100 includes a noise canceling processing unit 101 and a control unit 102. A plurality of microphones 111 are connected to the signal processing apparatus 100 via a plurality of AD (Analog/Digital) converters 113 and a plurality of microphone amplifiers 112. Further, a plurality of speakers 116 via a plurality of DA (Digital/Analog) converters 114 and a plurality of power amplifiers 115 are connected.

Further, the sound source 130 via a digital I/F 121 is connected to the signal processing apparatus 100. Note that the sound source 130 and the digital I/F 121 are not necessarily connected to each other. Furthermore, the synchronization circuit 140 is connected to the signal processing apparatus 100.

A plurality of microphones 111 via a plurality of microphone amplifiers 112 and a plurality of AD converters 113 is connected to the noise canceling processing unit 101. Further, a plurality of speakers 116 via a plurality of DA converters 114 and the power amplifier 115 is connected to the noise canceling processing unit 101. Thus one or more inputs and the one or more outputs may be connected to the noise canceling processing unit 101. Thus, the signal processing apparatus 100 is configured as a multi-input and multi-output apparatus. The signal processing apparatus 100 may reduce noise in a space (hereinafter referred to as a processing range) to be subjected to noise canceling processing by using a plurality of inputs and a plurality of outputs.

The microphone 111 collects sound and noise within the processing range that is subject to noise reduction by the signal processing apparatus 100. The audio signal based on the sound collection result by the microphone 111 is supplied to the AD converter 113, the gain being adjusted by the microphone amplifier 112. The AD converter 113 converts an audio signal, which is an analog signal, into a digital signal and supplies it to the noise canceling processing unit 101. The microphone 111 corresponds to an input unit in the claims.

The noise canceling processing unit 101 includes a digital filter for generating a noise reduction audio signal (hereinafter, referred to as a cancellation signal.). The noise canceling processing unit 101, using the digital audio signal supplied, generates a cancellation signal of characteristics corresponding to the filter coefficient as a predetermined parameter. The noise canceling processing unit 101 supplies a cancellation signal to a plurality of DA converters 114. Alternatively, the noise canceling processing unit 101 may be supplied to a plurality of DA converters 114 by generating a cancellation signal obtained by inverting the phase of the digital audio signal supplied. The control unit 102 controls the entire signal processing apparatus 100 and each unit, and further controls and manages communication between the signal processing apparatus 100 that is connected. The noise canceling processing unit 101 and the control unit 102 are each constituted by a DSP (Digital signal processing apparatus) or the like.

Incidentally, the signal processing apparatus 100 is constituted by a program. The program may be installed in advance in a processor such as a DSP or in a computer for performing signal processing. The program may be distributed via download, a storage medium, or the like to be installed by the user. In addition, the signal processing apparatus 100 may be implemented not only by a program, but also by a combination of dedicated devices, circuits, and the like by hardware having the functions.

The DA converter 114 converts the supplied cancellation signal into an analog signal. The DA converter 114 supplies a cancellation signal to the power amplifier 115. The power amplifier 115 then supplies a cancellation signal to the speaker 116. The speaker 116 outputs a cancellation signal. Thus, noise in the processing range may be reduced. The speaker 116 corresponds to an output unit in the claims.

The sound source 130 may also provide an audio content signal via a digital I/F 121 to the noise canceling unit 101. The sound source 130 is a music player, a DVD player, Blu-ray (registered trademark) player, a variety of media players such as car stereos. The audio content signal supplied from the sound source 130 is an audio signal reproduced by the media player. The user listens to this audio content signal as audio content within the processing range of noise canceling by the signal processing apparatus 100.

When the user listens to the audio content from the sound source 130 in the processing range of the signal processing apparatus 100, the audio content and noise reproduced from the sound source 130 are input to the microphone 111 in the processing range. The noise canceling processing unit 101 removes the audio content from the audio content and the noise signal using the audio content signal supplied through the digital I/F 121. Thus, the noise canceling processing unit 101 generates a signal of only noise. The noise canceling processing unit 101 generates a cancellation signal from the signal of only noise, and outputs it from the speaker 116.

Thus, only the noise may be reduced without affecting the audio content reproduced from the sound source 130 within the processing range.

The signal processing system includes the plurality of signal processing apparatuses 100 connected to each other. In this case, the synchronization circuit 140 generates and supplies a click signal for synchronizing all the plurality of signal processing apparatuses 100 connected.

The plurality of signal processing apparatuses 100 thus configured is daisy-chain connected by a dedicated bus 150. Thus, it is possible to constitute a signal processing system including the plurality of signal processing apparatuses 100. Therefore, it is possible to increase the size of the signal processing system in accordance with the size of the processing range which is the target of the noise canceling processing. Communication on the dedicated bus 150 enables transfer of various data such as control information, audio signals, cancellation signals, and the like.

The present technology is available in any environment for the purpose of reducing noise in a space. For example, the present technology is applied to a room of a house. Thus, it is possible to reduce noise entering the room from the outside of the house and noise generated inside the room. Then, the signal processing apparatuses are daisy-chain connected according to the size of the room to adjust the scale of the signal processing system. Thus, it is possible to appropriately reduce noise even large rooms. It is also possible to apply the present technology to the vehicle to reduce noise from the outside of the vehicle. It is also possible to reduce the noise generated inside the vehicle.

When using the signal processing apparatuses 100 in such a room or vehicle, there are cases where speakers for audio content output and speakers for cancellation signal output are used in common. In such a case, only the noise is reduced, and the audio content output from the speaker is not reduced. To this end, the sound source 130 is connected to the signal processing apparatus 100 via the digital I/F 121. The sound source 130 supplies the audio content signal to the noise canceling processing unit 101. Then, the noise canceling processing unit 101 removes the audio content signal from the signal of the audio content and the noise collected by the microphone. Thus the noise canceling processing unit 101 generates a signal of only noise. The noise canceling processing unit 101 is used to generate a cancellation signal from the signal of only noise. This makes it possible to reduce only the noise without reducing the audio content from the sound source 130 within the processing range.

When the plurality of signal processing apparatuses 100 are connected by a dedicated bus 150 to form a signal processing system, audio content signals must also be transferred between the signal processing apparatuses via a dedicated bus 150. As the audio content, a voice call of a telephone and a voice command may also be used.

In the following description, the module means a configuration in which a microphone amplifier, an AD converter, a DA converter, and a power amplifier are connected to the signal processing apparatus. Microphones and speakers are connected to the module.

Next, the classification of the noise canceling system will be described. The noise canceling system may be mainly divided into the feedforward system and the feedback system.

According to the feedforward system, noise is collected by a microphone to obtain a noise signal, the noise signal is subjected to a predetermined signal processing to generate a cancellation signal, and the cancellation signal is output from a speaker or the like. This reduces noise. According to the feedforward system, a reference microphone for collecting noise is required.

According to the feedback system, noise is collected by a microphone together with sound reproduced within the processing range, only noise components are extracted from the audio signal, and the audio signal is subjected to predetermined signal processing to generate a cancellation signal. Then, the cancellation signal is output from a speaker or the like. This reduces the noise. According to the feedback system, an error microphone for obtaining and feeding back the error of noise reduction (residual noise) is required.

In addition, there are a first feedback system, a second feedback system, and a third feedback system in the feedback system.

Figure 2:
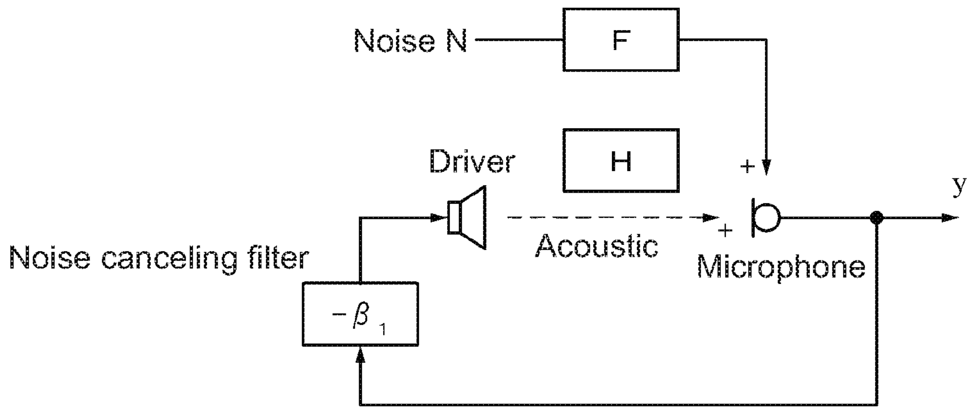
FIG. 2 A diagram illustrating a first feedback system.

The first feedback system maximizes the denominator of the sensitivity function based on classical control engineering, as shown in FIG. 2. This is a technique for reducing noise.

Figure 3:
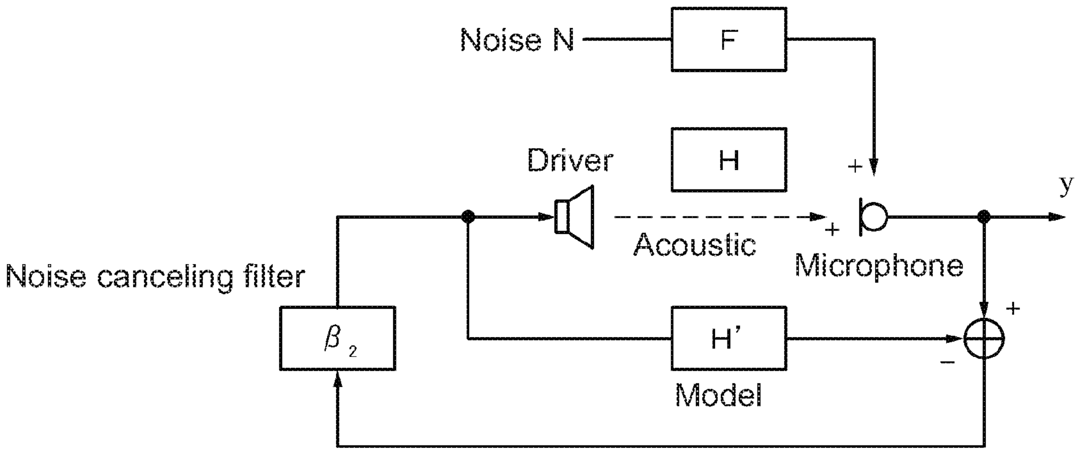
FIG. 3 A diagram illustrating a second feedback system.

The second feedback system is a method in which an internal model is introduced into a feedback loop as shown in FIG. 3, and the numerator of the sensitivity function is minimized, for reducing noise.

Figure 4:
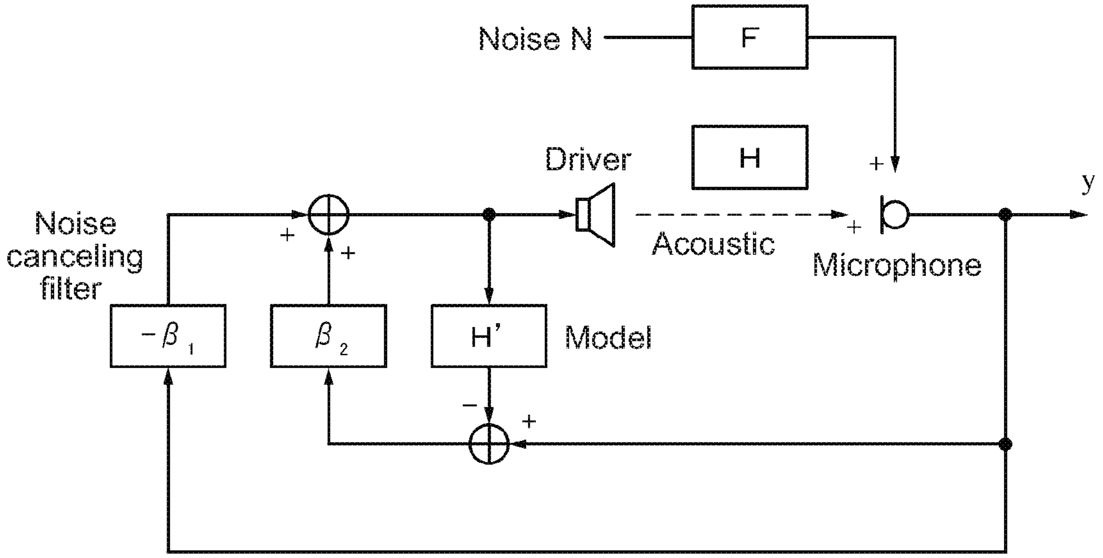
FIG. 4 A diagram illustrating a third feedback system.

The third feedback system is a combined method of the first and second methods, as shown in FIG. 4.

If more accurate noise canceling processing is required, these methods may be combined to enhance the performance of the noise canceling.

[1-2. Connection of Signal Processing Apparatuses]

Figure 5:
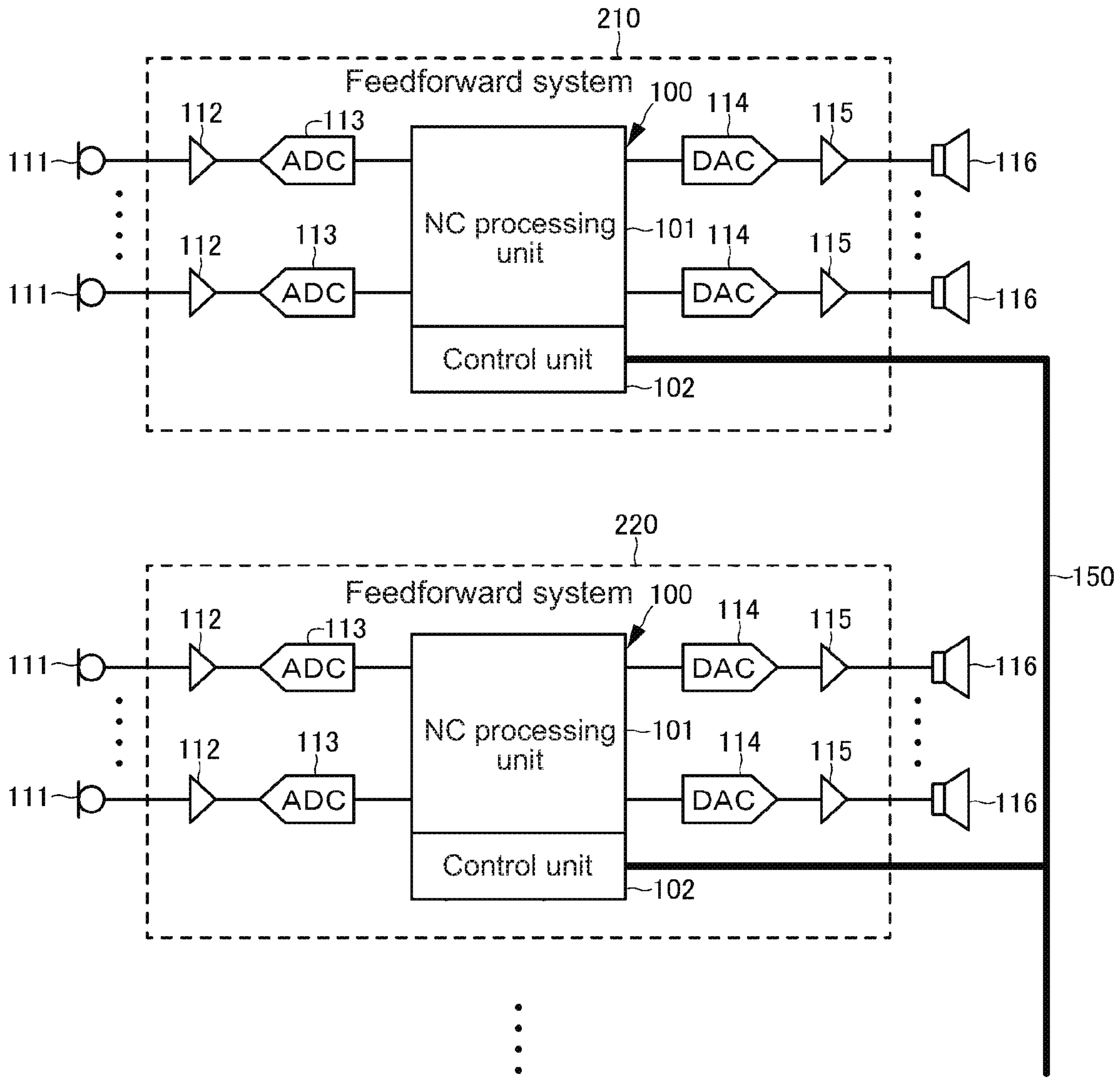
FIG. 5 A diagram illustrating a connection of signal processing apparatuses of the feedforward system.

In FIG. 5, the plurality of signal processing apparatuses 100 that performs feedforward system noise canceling is daisy-chain connected. In this example, this constitutes a multi-input and multi-output signal processing system. A signal processing apparatus 100 is connected by a dedicated bus 150. Thus, the module 210, the module 220, . . . are connected to constitute a signal processing system of multi-inputs and multi-outputs.

Figure 6:
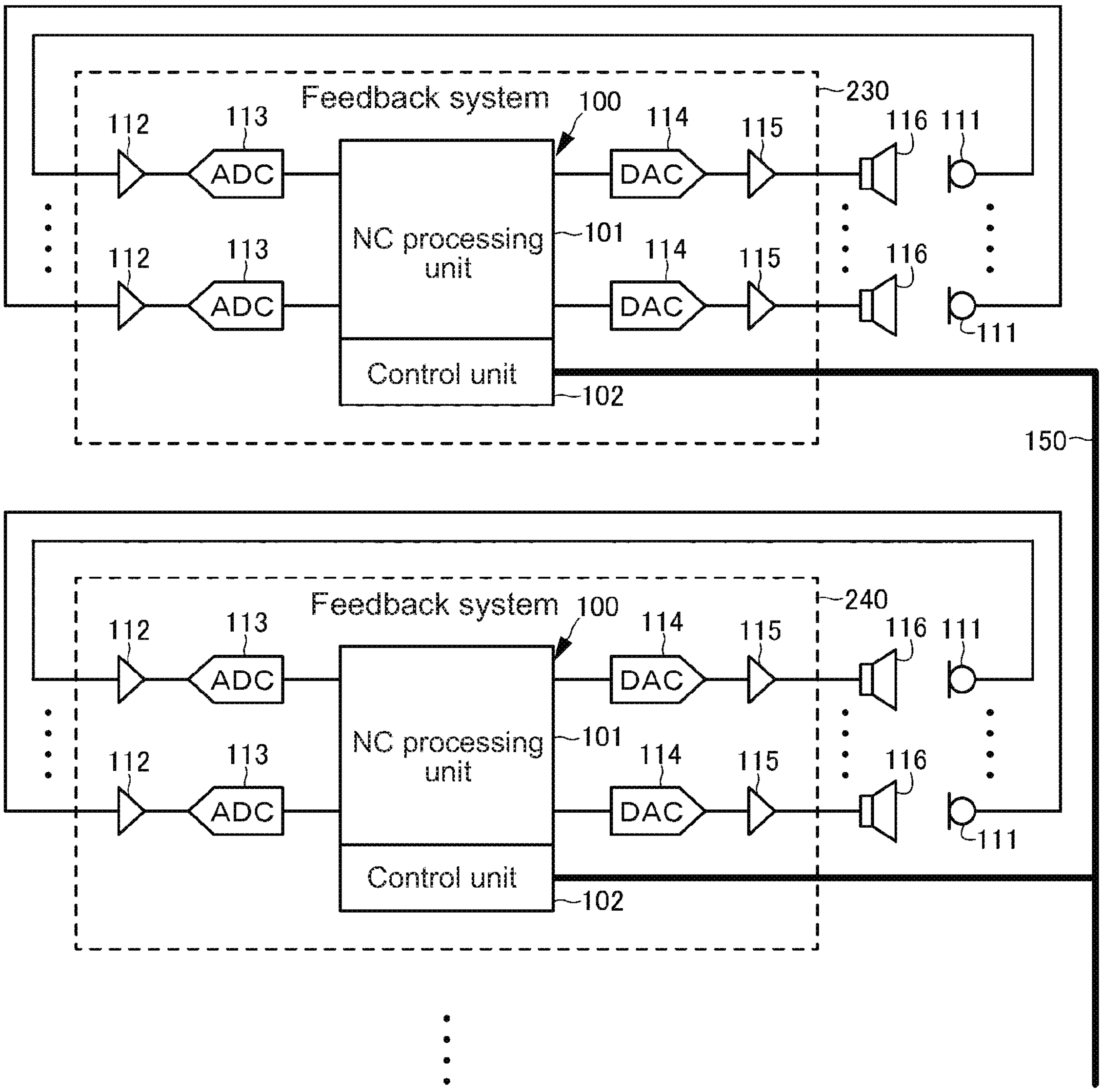
FIG. 6 A diagram illustrating a connection of signal processing apparatuses of the feedback system.

Further, in FIG. 6, the plurality of signal processing apparatuses 100 is daisy-chain connected for performing the feedback system noise canceling. It is an example of constituting a signal processing system of multi-inputs and multi-outputs accordingly. A signal processing apparatus 100 is connected by a dedicated bus 150. Thus, the module 230, the module 240, . . . are connected to constitute a signal processing system of the input and output.

In this way, the plurality of signal processing apparatuses 100 is daisy-chain connected using the dedicated bus 150, even in the case of noise canceling of the feedforward type or the feedback type noise canceling. As a result, the number of inputs and the number of outputs may be increased. Furthermore, it is possible to increase the number of noise canceling processing units 101 for performing the noise canceling processing. As a result, the processing range in which noise canceling may be performed may be expanded. Therefore, the scale of the signal processing system may be expanded according to the expansion of the processing range. Furthermore, it is possible to improve the noise canceling performance.

Figure 7:
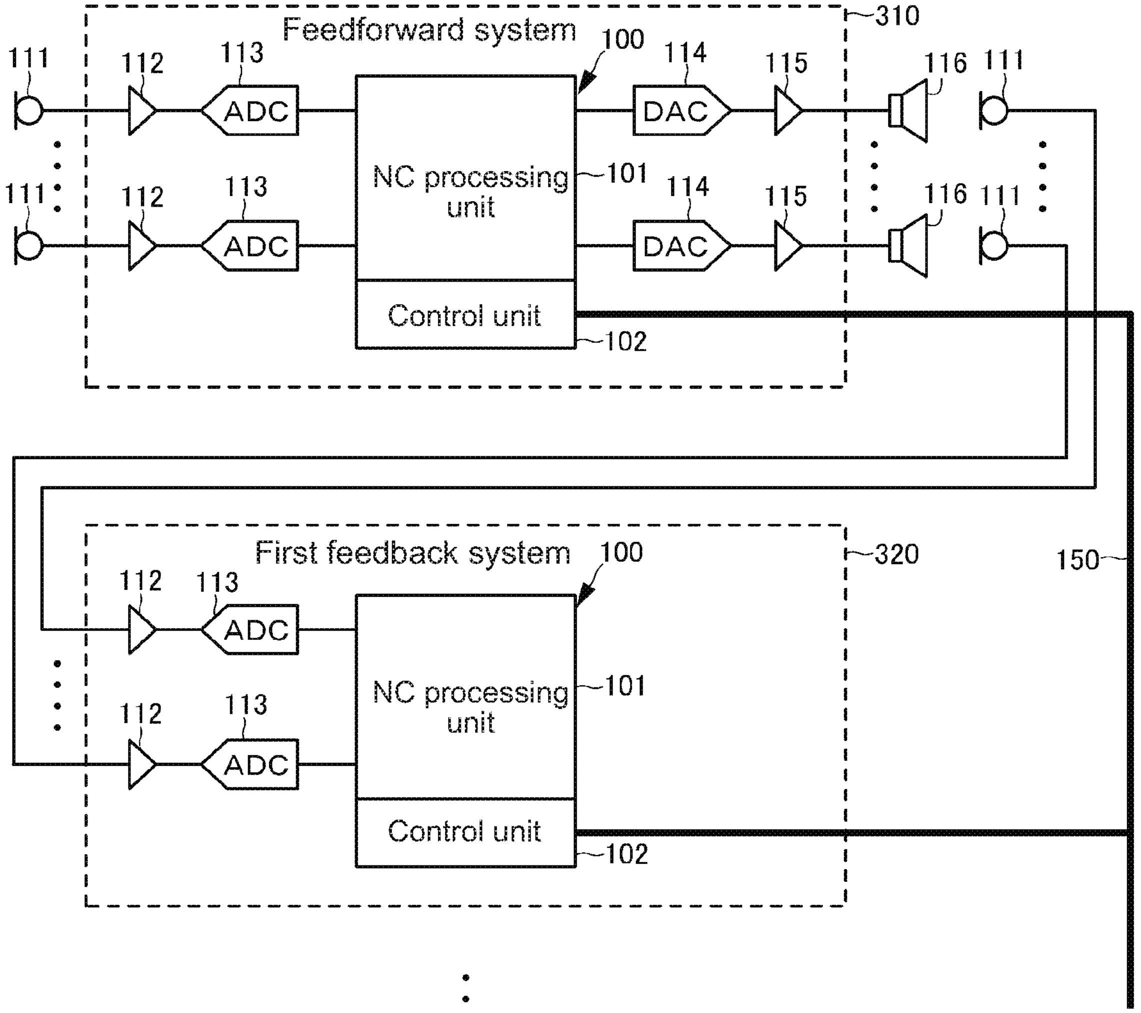
FIG. 7 A diagram for explaining the connection of the signal processing apparatus of the feedforward system and the signal processing apparatus of the feedback system.

In FIG. 7, the feedforward signal processing apparatus 100 and a first feedback signal processing apparatus 100 are daisy-chain connected. In this example, a plurality of modules 310, 320, . . . are connected to form a multi-input and multi-output signal processing system. A microphone 111 connected to the feedforward signal processing apparatus 100 serves as a reference microphone that collects noise. The microphone 111 connected to the signal processing apparatus 100 of the first feedback system also functions as an error microphone that obtains an error in noise reduction.

In FIG. 7, the signal processing apparatus 100 of the feedforward system and the signal processing apparatus 100 of the first feedback system are daisy-chain connected, and the cancellation signal may be transmitted and received. Therefore, the speaker for outputting the cancellation signal may be connected to either one of the signal processing apparatus 100. In FIG. 7, the speaker 116 is connected to the signal processing apparatus 100 of the feedforward system. Alternatively, a speaker may be connected to the signal processing apparatus 100 of the first feedback system.

Figure 8:
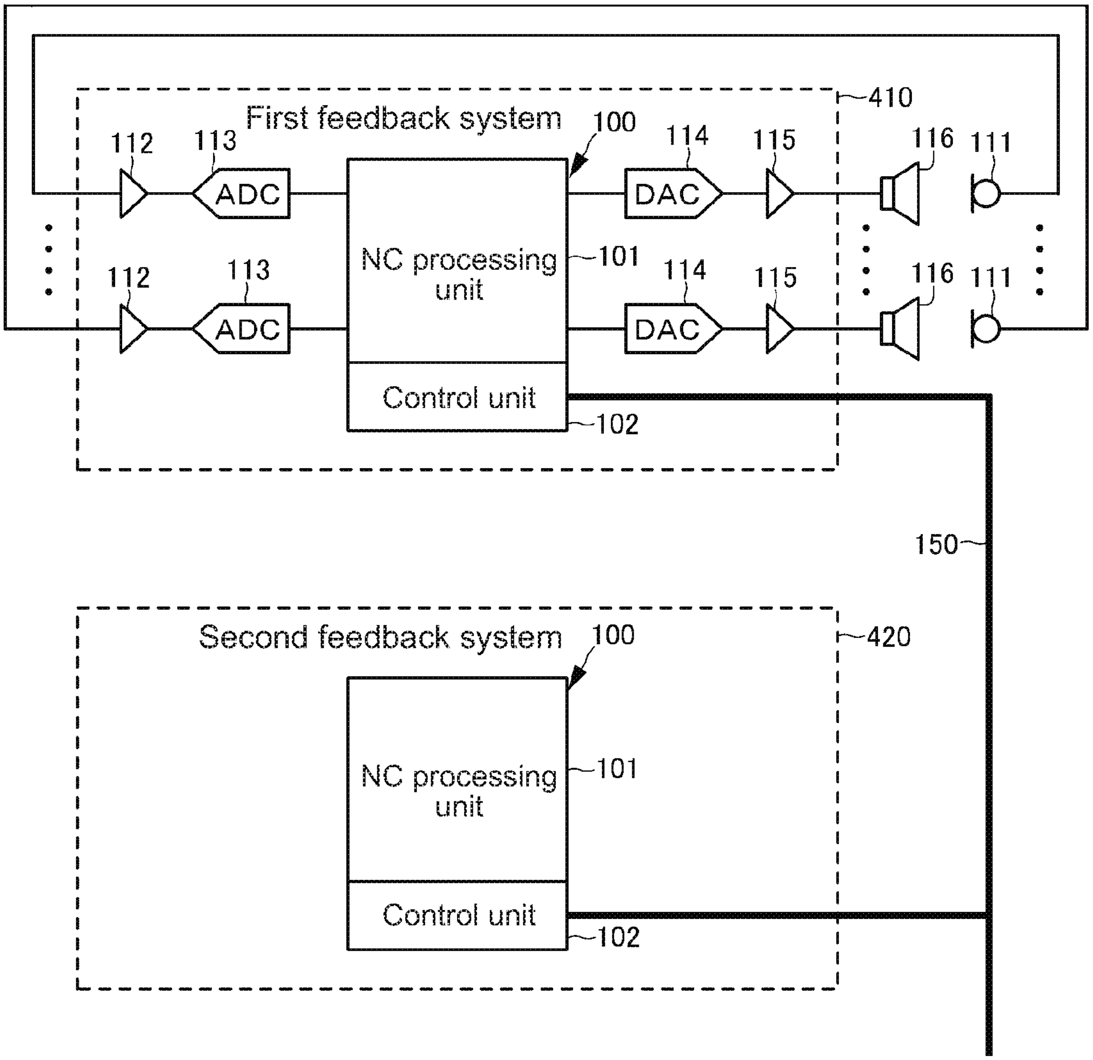
FIG. 8 A diagram for explaining the connection of the signal processing apparatus of the first feedback system and the signal processing apparatus of the second feedback system.

In FIG. 8, the signal processing apparatus 100 of the first feedback system and the signal processing apparatus 100 of the second feedback system are daisy-chain connected. In this example, a plurality of modules 410, 420, . . . are connected to form a multi-input and multi-output signal processing system. The combination of the first feedback system and the second feedback system is an example of a third feedback system. Both the first and second feedback systems are feedback systems. Therefore, the microphone and the speaker may be shared by the signal processing apparatus 100 of the first feedback system and the signal processing apparatus 100 of the second feedback system. Therefore, the microphone 111 and the speaker 116 may be connected to either the signal processing apparatus 100 of the first feedback system or the signal processing apparatus 100 of the second feedback system.

Figure 9:
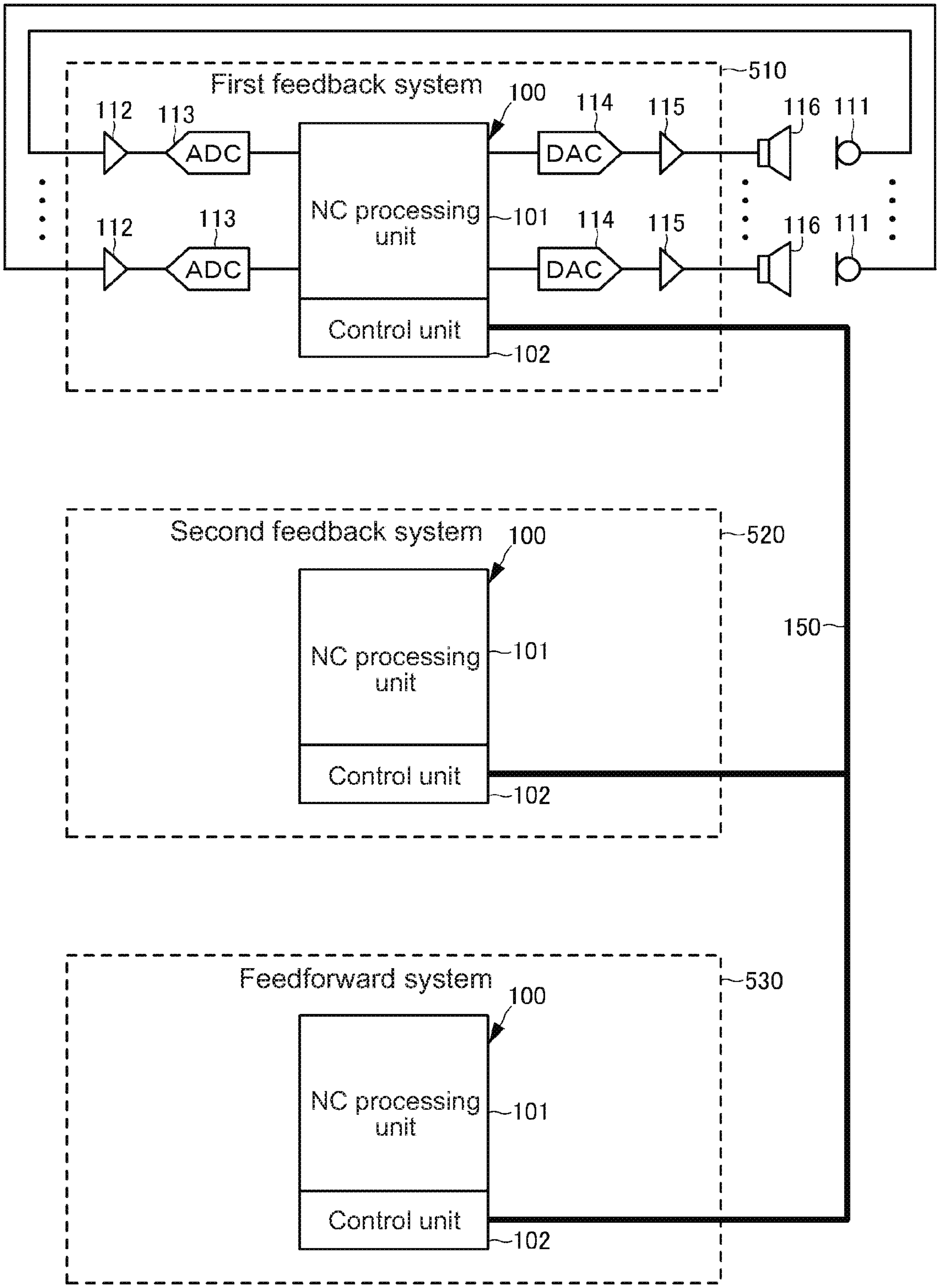
FIG. 9 A diagram for explaining the connection of the signal processing apparatus of the feedforward system and the signal processing apparatus of the third feedback system.

In FIG. 9, the feedforward signal processing apparatus 100 and the signal processing apparatus 100 of the third feedback system are daisy-chain connected. In this example, a plurality of modules 510, 520, and 530 are connected to form a multi-input and multi-output signal processing system. In FIG. 9, a speaker 116 is connected to the signal processing apparatus 100 of the first feedback system. A cancellation signal is exchanged by communication on the dedicated bus 150. Therefore, a speaker may be connected to any signal processing apparatus 100.

FIG. 7 to FIG. 9 are only examples of connections of a noise canceling system. The combination of connections is not limited to these. The combination and number of noise canceling systems to be connected may be determined in accordance with the magnitude of the noise, the direction of arrival of the noise, and the like.

Figure 10:
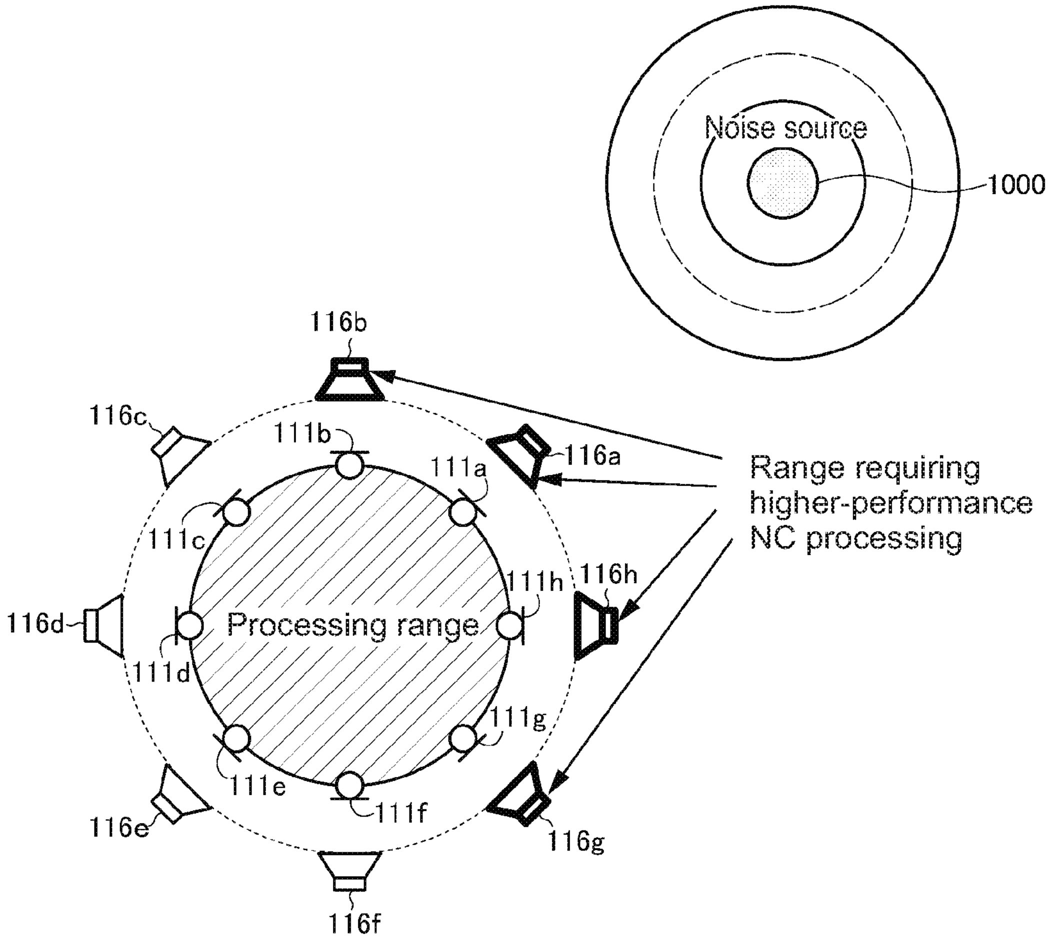
FIG. 10 A diagram for explaining the direction of arrival of noise from the noise source.

In the processing range to be subjected to the noise canceling processing, the noise is not always uniformly distributed. For example, as shown in FIG. 10, the microphones 111*a* to 111*h* and the speakers 116*a* to 116*h* are connected to a plurality of modules, respectively, and arranged in a circular shape. The direction of arrival of noise from the noise source 1000 to the microphones 111*a* to 111*h* and the speakers 116*a* to 116*h* may be concentrated in a particular direction. Therefore, the signal processing apparatuses 100 of the plurality of noise canceling systems are connected in a range requiring a higher-performance noise canceling processing, the range being closer to the noise source 1000. The plurality of signal processing apparatuses 100 of the plurality of noise canceling systems as described in FIGS. 7 to 9 is connected for the direction of arrival of the noise. Thus it may be possible to perform a high-performance noise canceling processing. Incidentally, for convenience of illustration in FIG. 10, only a microphone and a speaker connected to the module will be described.

Figure 11:
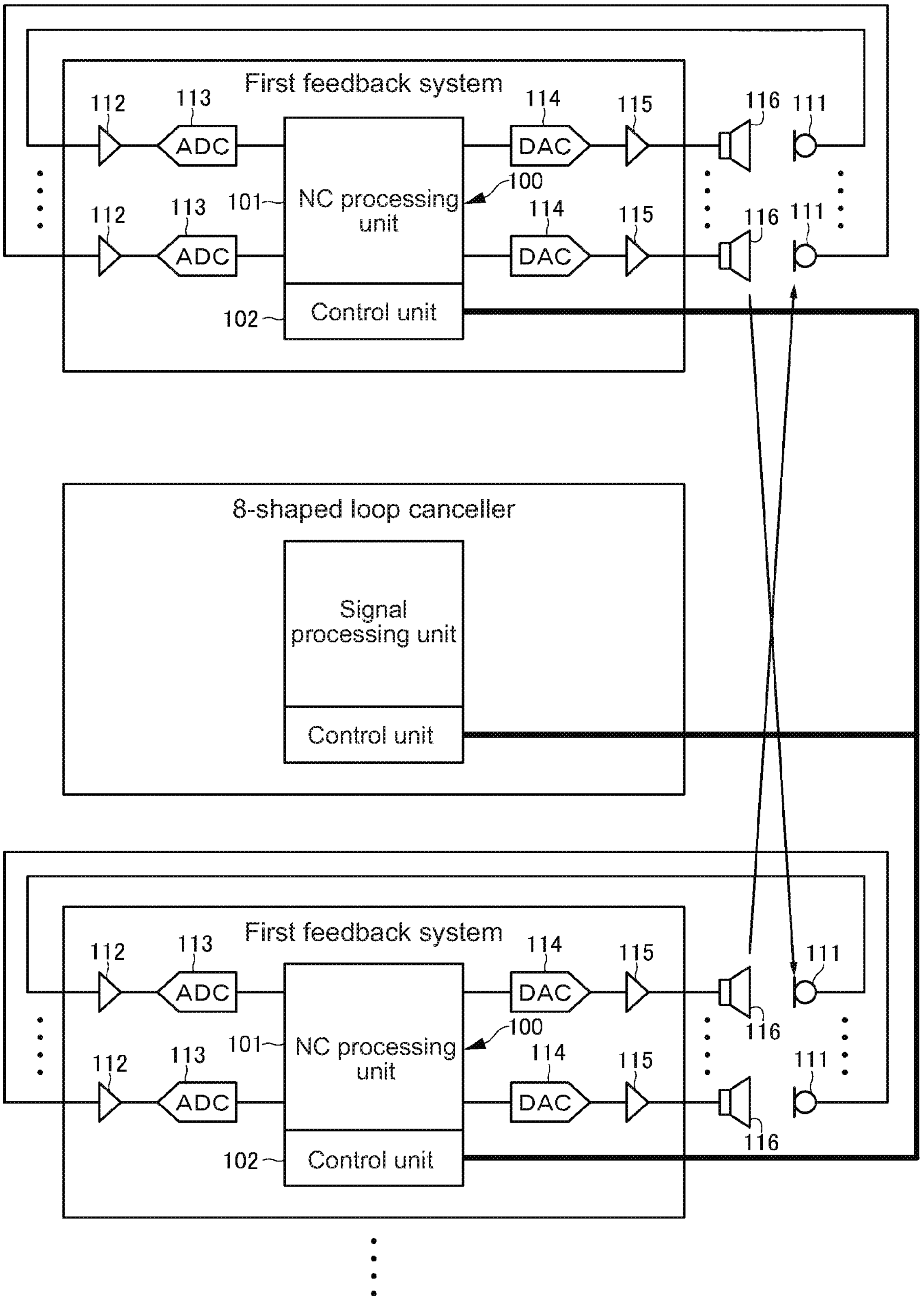
FIG. 11 An explanatory diagram of a case of the connection of the signal processing apparatuses of the first feedback system as an 8-shaped loop canceller.

Further, FIG. 11 is an example of using the signal processing apparatus 100 as an 8-shaped loop canceller for connecting the first feedback systems. International Publication No. WO 2017/175448 discloses an 8-shaped loop canceller. The signal processing apparatus 100 is applied to an 8-shaped loop canceller. As a result it is possible to reduce mutual interference between modules.

Figure 12:
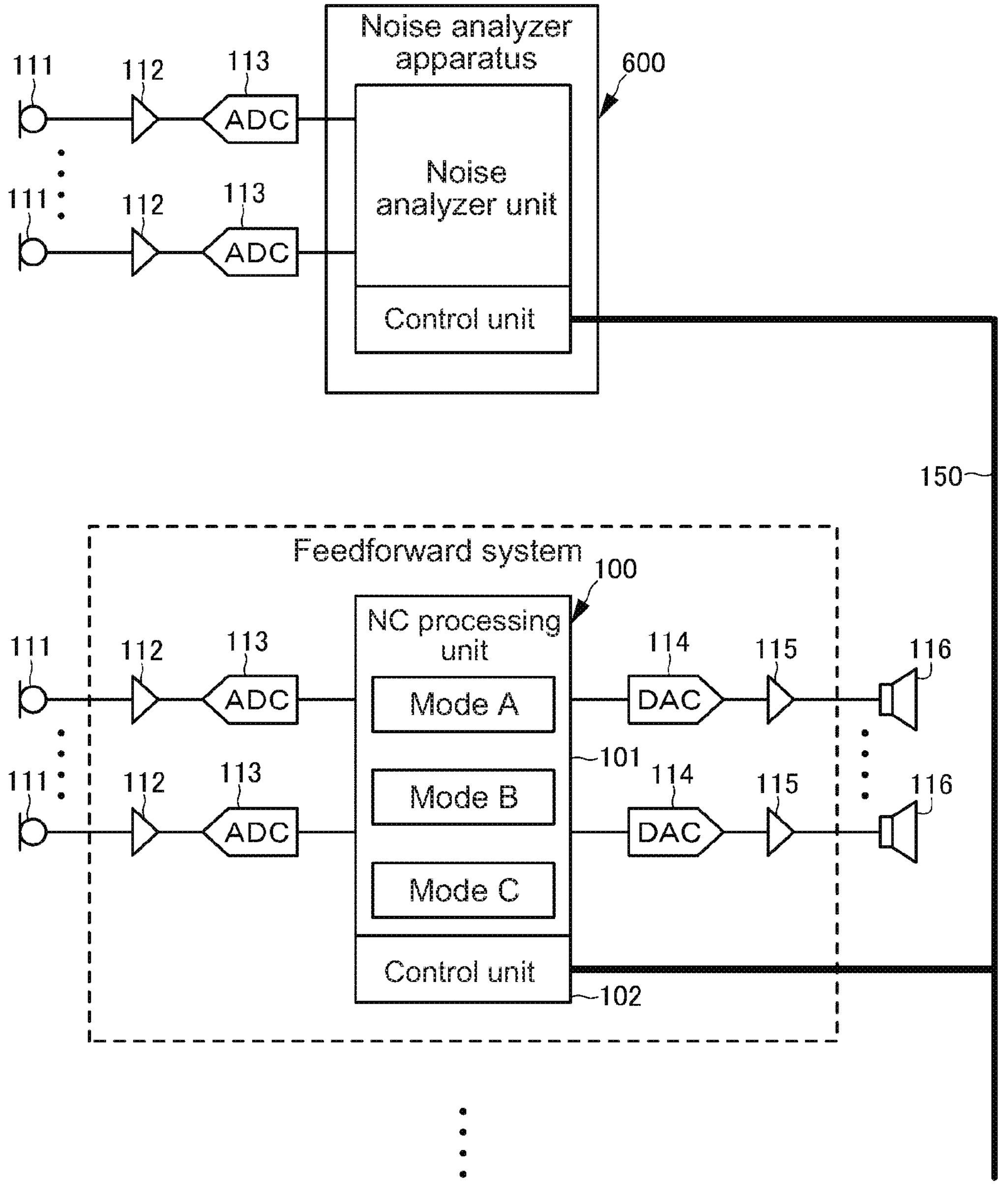
FIG. 12 A diagram illustrating a connection between the noise analyzer and the signal processing apparatus.

Furthermore, as shown in FIG. 12, a noise analyzer apparatus 600 may be connected to the signal processing apparatus 100. In FIG. 12, the noise analyzer apparatus 600 is supplied with the audio signal collected by the microphone 111, and the noise analyzer apparatus 600 performs a predetermined audio analysis process on the audio signal. Thus, the noise analyzer apparatus 600 obtains analysis information such as the type of noise, the level of noise, the direction of arrival of noise, and the power spectrum of noise. Then, the noise analyzer apparatus 600 supplies the analysis information to the signal processing apparatus 100 via the dedicated bus 150. Thus, the signal processing apparatus 100 selects a combination of noise canceling systems based on the analysis information. The signal processing apparatus 100 selects a mode of noise cancellation. The combinations of the noise canceling systems have been described with reference to FIGS. 5, 6, 7, 8 and 9.

Selection of the mode of noise cancellation is to select an in-flight mode, an office mode, an outdoor mode, or the like in the signal processing apparatus 100. In each mode, a digital filter, a filter coefficient, and the like are set in advance so that appropriate noise canceling may be performed in accordance with the size of the noise and the type of noise.

As described above, the noise canceling processing units are daisy-chain connected. Thus it is possible to enlarge the processing range, and improve the performance of the noise canceling.

1-3. Data Transfer

[1-3-1. First Example of a Circular Array]

Figure 13:
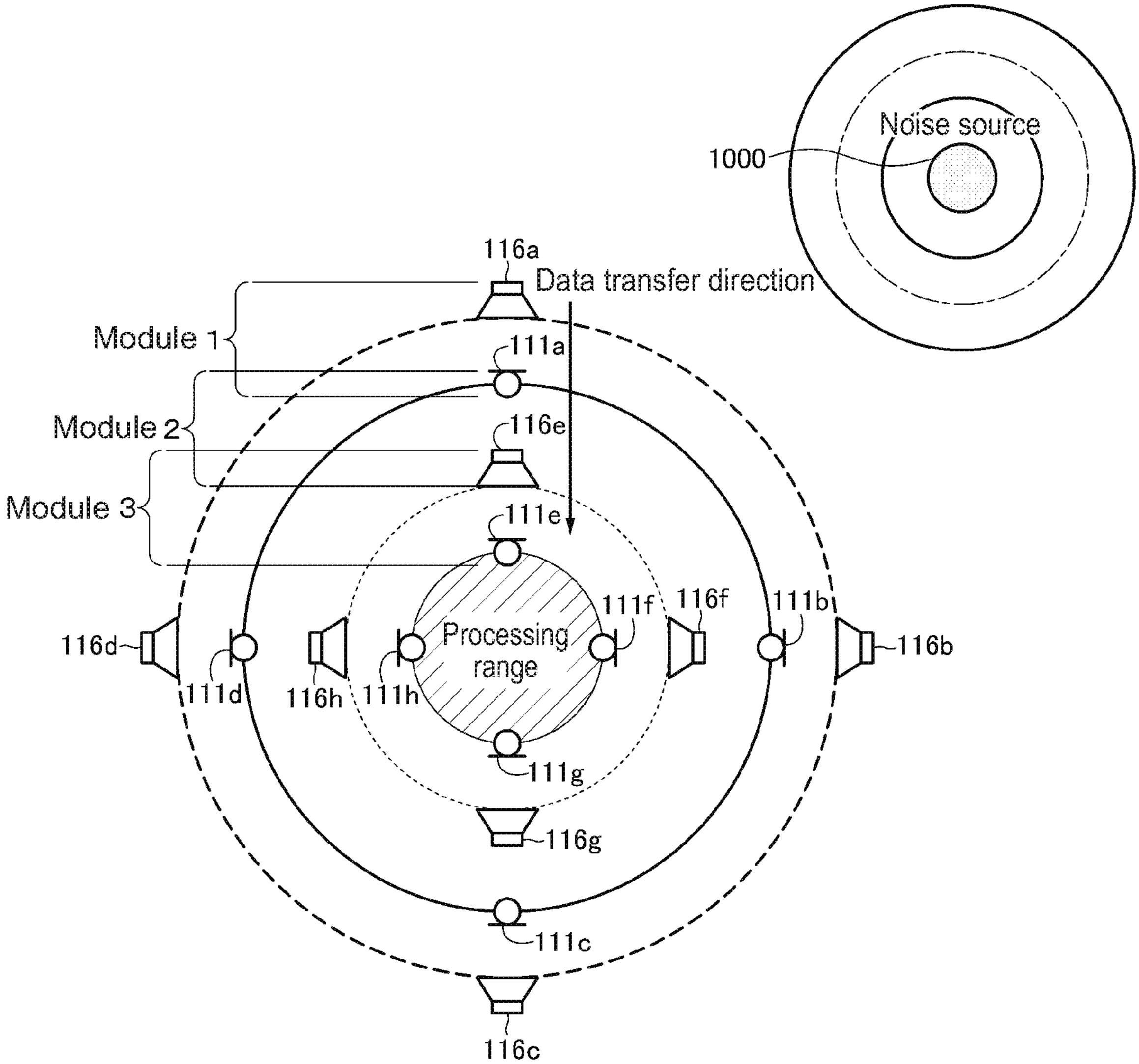
FIG. 13 A diagram showing a case where the module is arranged in a circular array and a noise source is present outside the circular array.

Next, a first example of the data transfer processing between the signal processing apparatuses will be described. As shown in FIG. 13, the processing range is a region inside a specific closed space. In order to reduce noise in the processing range, a plurality of modules are arranged so as to surround the processing range. The plurality of modules are arranged in a plurality of circular arrays. In FIG. 13, a noise source 1000 is present outside the plurality of circular arrays. In FIG. 13, only the microphones 111*a* to 111*h* and the speakers 116*a* to 116*h* connected to the module are shown for convenience of illustration. The signal processing apparatus 100, the DA converter 114, the AD converter 113, the microphone amplifier 112, the power amplifier 115, and the like constituting the module are not shown.

Among the microphones 111*a* to 111*h* and the speakers 116*a* to 116*h* arranged in a plurality of circular arrays, a speaker 116*a*, a microphone 111*a*, a speaker 116*e*, and a microphone 111*e* positioned on a straight line will be described. The speaker 116*a* and the microphone 111*a* are connected to the module 1. The microphone 111*a* and the speaker 116*e* are connected to the module 2. Further, a speaker 116*e* and a microphone 111*e* are connected to the module 3. The module 1 performs noise cancellation of the feedback system. The module 2 performs noise cancellation of the feedforward system. The module 3 performs noise cancellation of the feedback system.

When the noise source 1000 is outside of the plurality of circular arrays, the noise comes from outside to inside of the plurality of circular arrays. That is, the noise reaches the outside earlier than the inside of the plurality of circular arrays. Further, the level of the noise collected by the microphone 111*a* arranged outside is higher than the level of the noise collected by the microphone 111*e* arranged inside the plurality of circular arrays. Therefore, in order to perform noise canceling with high accuracy, the importance of the sound collected by the microphone 111*a* located at the outermost side of the plurality of circular arrays is high. As the microphones are toward the inside of the plurality of circular arrays, the importance of the sound is collected by the microphones is low. Therefore, it is preferable to transfer the audio signal acquired by the microphone 111*a* connected to the module 1 located outermost of the plurality of circular arrays to the inner module 2 and the module 3. That is, it may be transferred from the outside to the inside of the plurality of circular arrays, from the high importance circle to the low importance circle. Noise canceling processing in modules located inside the plurality of circular arrays also uses audio signals acquired by microphones connected to modules located outside the plurality of circular arrays.

Figure 14:
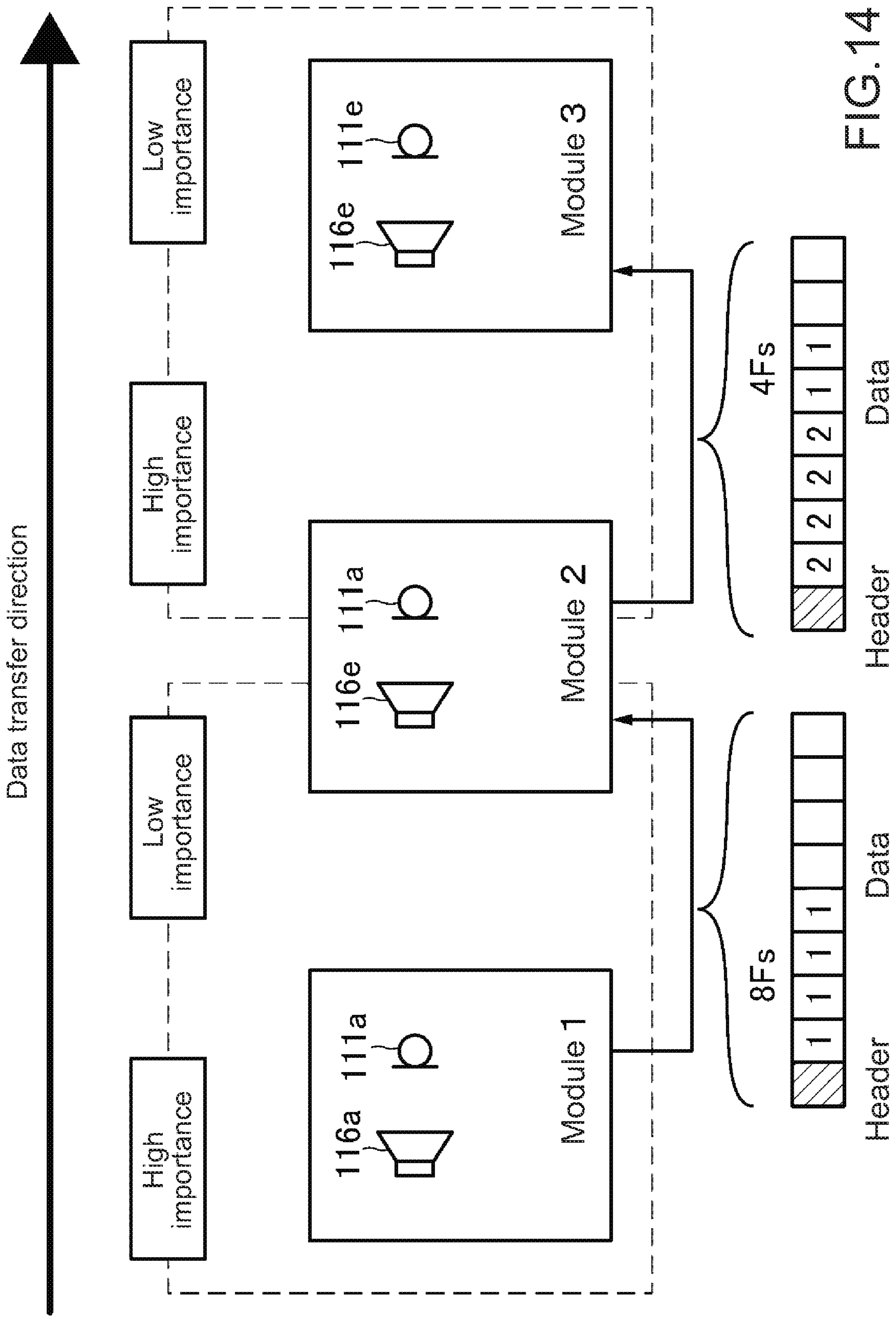
FIG. 14 An explanatory diagram of a data transfer in the example of FIG. 13.

FIG. 14 shows an outline of data transfer. FIG. 14 shows the relationship between the microphones and speakers arranged in the circular arrays shown in FIG. 13 by extracting the modules 1, 2, and 3 arranged in a straight line.

The microphone 111*a* is used as an error microphone in the module 1. On the other hand, the microphone 111*a* is used in the module 2 as a feed-forward reference microphone which may collect noise before it reaches the module. That is, this indicates that the importance is high because the module 1 is located outward with respect to the module 2 and is close to the noise source 1000. Thus, an audio signal is transferred from the outer module 1 to the module 2. The audio signal collected at a position close to the noise source 1000 may be used for noise canceling processing in a module far from the noise source. It is possible to improve the noise canceling effect.

Similarly, in the module 2 and the module 3, the module 2 is closer to the noise source 1000. Therefore, the importance of the audio signal acquired by the microphone 111*a* connected to the module 2 is high. Therefore, the audio signal is transferred from the module 1 to the module 2. Further, the audio signal is transferred from the module 2 to the module 3. Thus, it is possible to use the audio signal collected at a position close to the noise source 1000 in the noise canceling processing in a far module from the noise source. It is possible to improve the noise canceling effect.

Incidentally, the audio signal is transferred from the module close to the noise source 1000 to the module far from the noise source 1000. In this case, it is preferable to transfer the audio signal by lowering the sampling frequency, lowering the bit rate, or the like. As a result, the data size of the audio signal is reduced. It is possible to secure the resources of the signal processing apparatus 100, to increase the speed of transfer, and the like.

This technology increases the number of daisy-chain connected signal processing apparatuses. Thus, it is possible to increase the scale of the signal processing system according to the size of the processing range. As the scale of the signal processing system increases, the data transferred increases and the size of the data handled increases. Therefore, it is important to secure resources by reducing the data size in this way. The transfer from a module close to the noise source to a module far from the noise source is a transfer from a module having a high importance level to a module having a low importance level. For this reason, the sampling frequency and the bit rate are lowered. This does not affect the quality of the noise canceling even if the quality of the audio signal is deteriorated.

[1-3-2. Second Example of a Circular Array]

Figure 15:
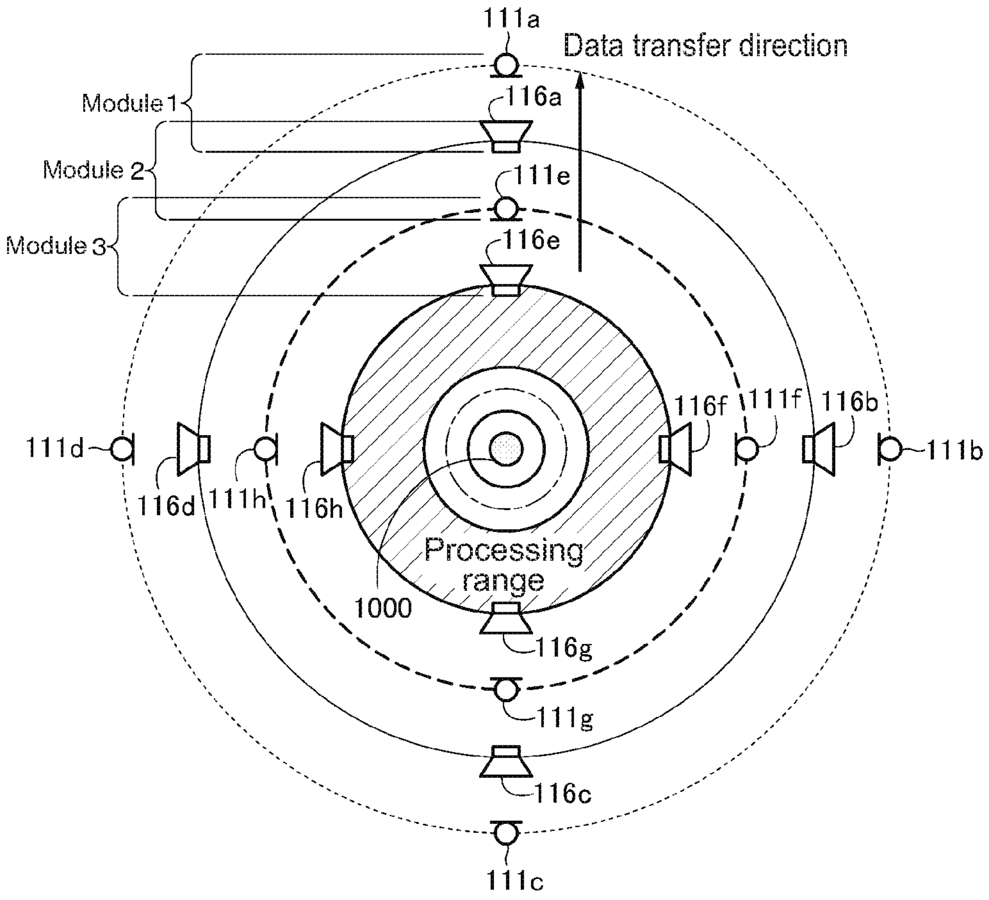
FIG. 15 A diagram illustrating the modules arranged in a circular array, with noise sources present in the circular array.

Next, a second example of the data transfer processing between the signal processing apparatuses will be described. As shown in FIG. 15, the processing range is a region inside a specific closed space. In order to reduce noise in the processing range, a plurality of modules are arranged so as to surround the processing range. The plurality of modules are arranged in a plurality of circular arrays. In FIG. 15, a noise source 1000 is present outside the processing range. In FIG. 15, only the microphones 111*a* to 111*h* and the speakers 116*a* to 116*h* connected to the module are shown for convenience of illustration. The signal processing apparatus 100, the DA converter 114, the AD converter 113, the microphone amplifier 112, the power amplifier 115, and the like constituting the module are not shown.

Among the microphones 111*a* to 111*h* and the speakers 116*a* to 116*h* arranged in a plurality of circular arrays, a speaker 116*a*, a microphone 111*a*, a speaker 116*e*, and a microphone 111*e* positioned on a straight line will be described. The speaker 116*a* and the microphone 111*a* are connected to the module 1. The microphone 111*a* and the speaker 116*e* are connected to the module 2. Further, a speaker 116*e* and a microphone 111*e* are connected to the module 3. The module 1 performs noise cancellation of the feedback system. The module 2 performs noise cancellation of the feedforward system. The module 3 performs noise cancellation of the feedback system.

When the noise source 1000 is inside of the plurality of circular arrays, the noise comes from inside to outside of the plurality of circular arrays. That is, the noise reaches the inside earlier than the outside of the plurality of circular arrays. Further, the level of the noise collected by the microphone 111*e* arranged inside is higher than the level of the noise collected by the microphone 111*a* arranged outside the plurality of circular arrays. Therefore, in order to perform noise canceling with high accuracy, the importance of the sound collected by the microphone 111*e* located at the innermost side of the plurality of circular arrays is high. As the microphones are toward the outside of the plurality of circular arrays, the importance of the sound is collected by the microphones is low. Therefore, it is preferable to transfer the audio signal acquired by the microphone 111*e* connected to the module 1 located innermost of the plurality of circular arrays to the outer modules 3. That is, it may be transferred from the inside to the inside of the plurality of circular arrays, from the high importance circle to the low importance circle. Noise canceling processing in modules located outside the plurality of circular arrays also uses audio signals acquired by microphones connected to modules located inside the plurality of circular arrays.

Figure 16:
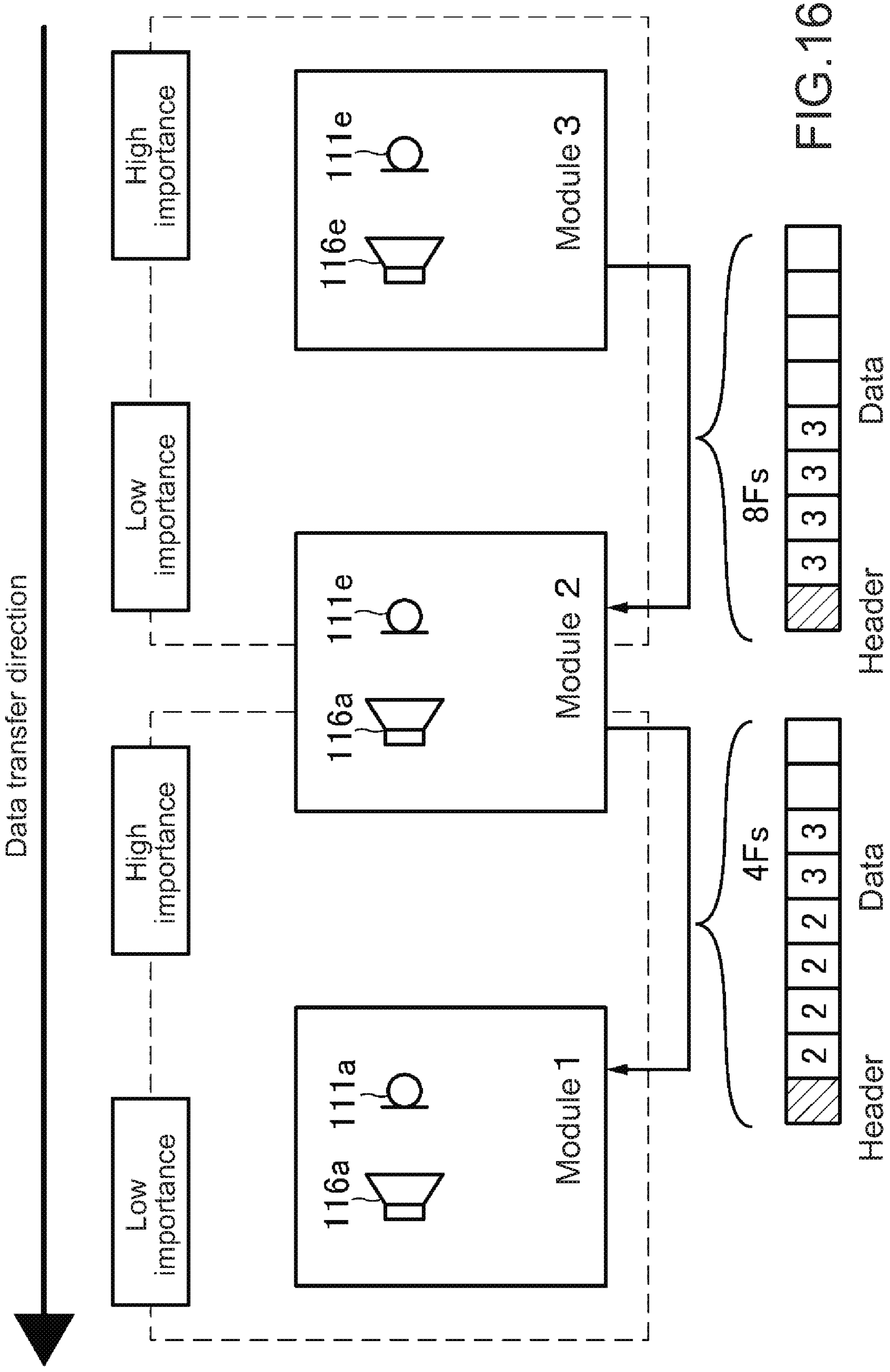
FIG. 16 A diagram illustrating a data transfer in the example of FIG. 15.

FIG. 16 shows an outline of data transfer. FIG. 16 shows the relationship between the microphones and speakers arranged in a circular array shown in FIG. 15 by extracting the modules 1, 2, and 3 arranged in a straight line.

The microphone 111*e* is used as an error microphone in the module 3. On the other hand, the microphone 111*e* is used in the module 2 as a feed-forward reference microphone. That is, this indicates that the importance is high because the module 3 is located inward with respect to the module 2 and is close to the noise source 1000. Thus, an audio signal is transferred from the inner module 3 to the module 2. The audio signal collected at a position close to the noise source 1000 may be used for noise canceling processing in a module far from the noise source. It is possible to improve the noise canceling effect.

Similarly, in the module 2 and the module 1, the module 2 is closer to the noise source 1000. Therefore, the importance of the audio signal acquired by the microphone 111*e* connected to the module 2 is high. Therefore, the audio signal is transferred from the module 3 to the module 2. Further, the audio signal is transferred from the module 2 to the module 1. Thus, it is possible to use the audio signal collected at a position close to the noise source 1000 in the noise canceling processing in a module far from the noise source. It is possible to improve the noise canceling effect.

Incidentally, the audio signal is transferred from the module close to the noise source 1000 to the module far from the noise source 1000. In this case, it is preferable to transfer the audio signal by lowering the sampling frequency, lowering the bit rate, or the like. This is the same as the example of FIG. 11.

Transfer of audio signals may be performed similarly for modules connected to other microphones and speakers than the microphone 111*a*, the speaker 116*a*, the microphone 111*e*, and the speaker 116*e* as shown in FIGS. 13 and 15.

Figures 17, 18:
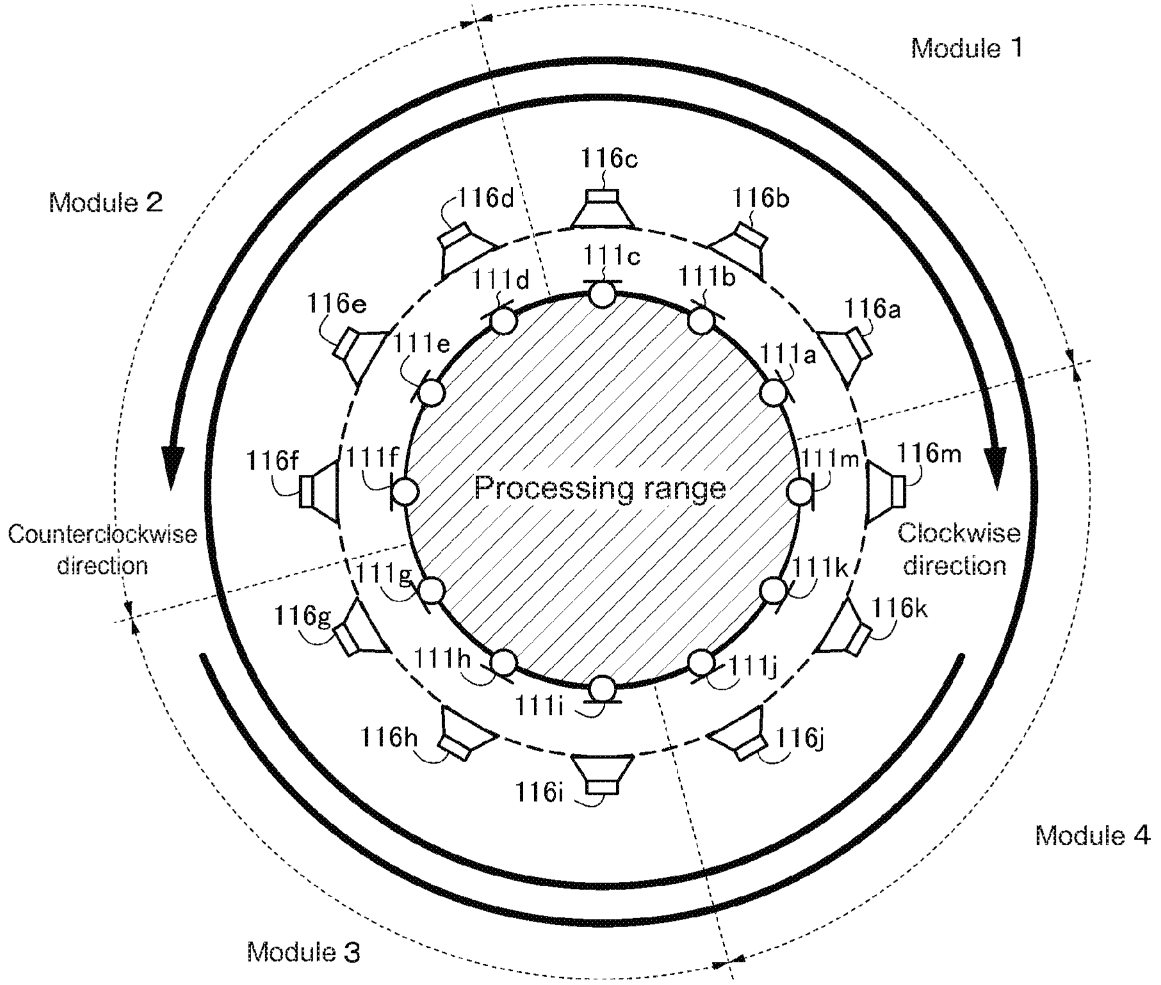
FIG. 17 A table showing the format of the data to be transferred.
FIG. 18 A diagram for explaining the direction of the data transfer.

FIG. 17 is a table showing the format of data transferred between daisy-chain connected signal processing apparatuses. Although the audio signal is transferred between the modules in the above description with reference to FIGS. 13 to 16, the data to be transferred is not limited to the audio signal. The data transferred between the signal processing apparatuses may be classified into a stream type and a bus type. Data in stream format include audio signals (input of a microphone), cancellation signals (output of a speaker), transfer functions, and the like. Data in stream format is required to be real-time.

On the other hand, the data in the bus system is control information or the like transmitted and received between the connected signal processing apparatuses, which is not required to have real-time characteristics, and may be classified into control data and data transmitted and received between the modules. Control data is data such as on-off control signal of the noise canceling processing. The data to be transmitted and received between modules includes the arrangement setting information of the module, the importance information according to the arrangement of the module, and the module number. The control data and the data transmitted and received between the modules both correspond to the control information in the claims.

As a specific example, information indicating the direction of arrival of the noise, information indicating the module to be connected when using a combination of different noise canceling systems, information indicating the arrangement relationship of the modules, etc., are not required to be real-time. For this reason, it is sufficient to transfer these information in the bus system.

[1-3-3. Direction of Data Transfer]

Next, the direction of data transfer will be described with reference to FIG. 18. As shown in FIG. 18, a plurality of microphones 111*a* to 111*m* and a plurality of speakers 116*a* to 116*m* connected to a module (not shown) are arranged in a circular shape. Those modules are connected by a dedicated bus.

The microphone 111*a*, the microphone 111*b*, the microphone 111*c*, the speaker 116*a*, the speaker 116*b*, and the speaker 116*c* are connected to the module 1. The microphone 111*d*, the microphone 111*e*, the microphone 111*f*, the speaker 116*d*, the speaker 116*e*, and the speaker 116*f* are connected to the module 2. The microphone 111*g*, the microphone 111*h*, the microphone 111*i*, the speaker 116*g*, the speaker 116*h*, and the speaker 116*i* are connected to the module 3. The microphone 111*j*, the microphone 111*k*, the microphone 111*m*, the speaker 116*j*, the speaker 116*k*, and the speaker 116*m* are connected to the module 4.

In this state, if the data transfer is performed in only one of the clockwise direction and the counterclockwise direction, the data transfer cannot be efficiently performed. Therefore, data is transferred in both clockwise and counterclockwise directions in the bidirectional bus in the clockwise and counterclockwise directions. In this way, data in the stream system, which requires real-time performance, may be transferred at low latency.

For example, if data may only be transferred clockwise and data needs to be transferred from the module 1 to the module 2, there is a delay in the transfer. On the other hand, there is a delay in the transfer when data transfer from the module 1 to the module 4 is required when data transfer may only be performed in the counter-clockwise direction. Therefore, bidirectional transfer is enabled by a bidirectional dedicated bus. Thus, when transferring data from the module 1 to the module 2, data may be transferred at a low delay. Also, when transferring from the module 1 to the module 4, data may be transferred with low latency.

[1-3-4. Packing in Data Transfer]

Next, a first example of packing in data transfer will be described with reference to FIG. 19. Packing in data transfer is a process of collecting data to be transferred when data is transferred between modules.

Figure 19:
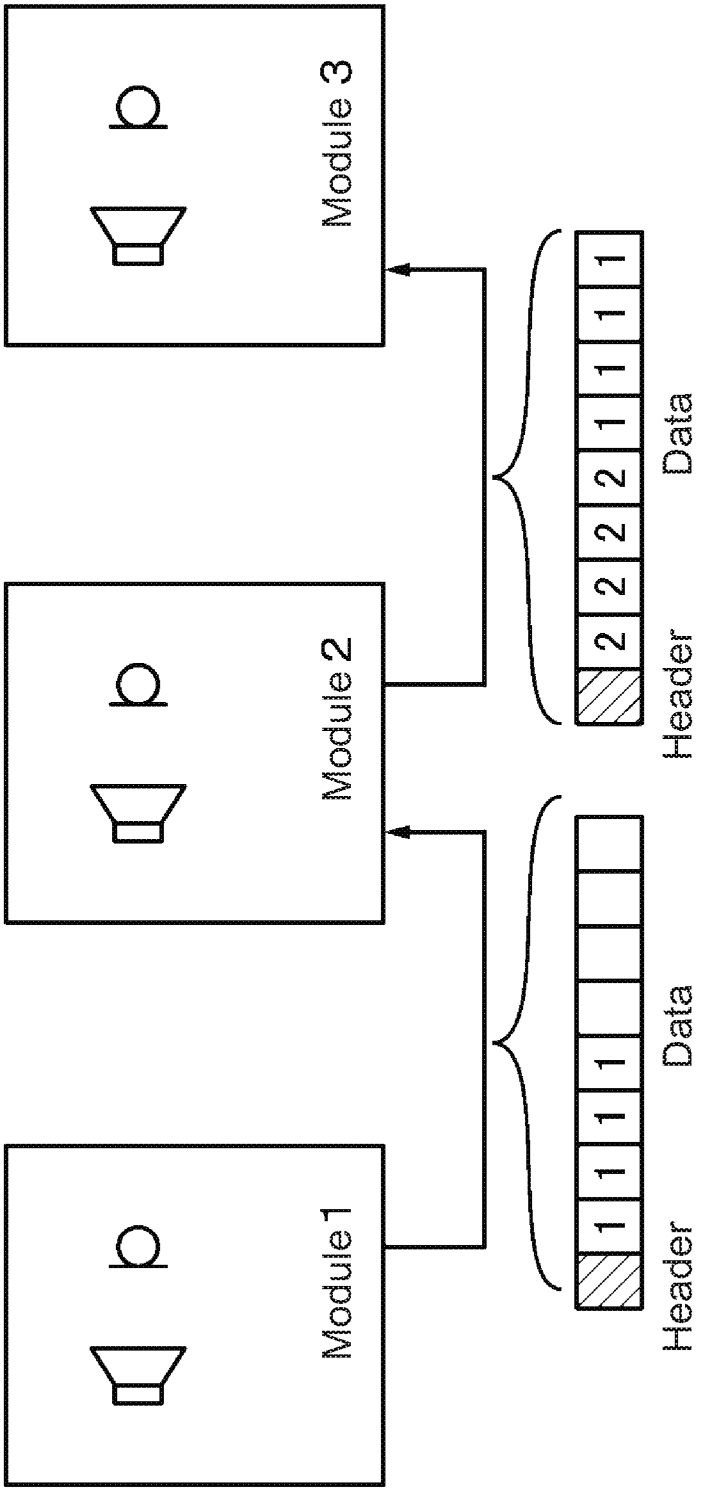
FIG. 19 A diagram illustrating a first example of packing in data transfer.

Data is transferred from the module 1 to the module 2 as shown in FIG. 19. In addition, data is transferred from the module 2 to the module 3. Note that numerical values assigned to data in FIG. 19 and FIG. 20 described later indicate data in each module. Data transferred from the module 1 to the module 2 includes data in the module 1. Data transferred from the module 2 to the module 3 includes data in the module 1 and data in the module 2.

The module 1 transfers data to the module 2. Then, the module 2 once pulls up the sent data. Next, the right shift is performed on the acquired data. In this way, resources are allocated so that the data of the module 2 may be inserted. Then, the data of the module 2 is inserted at the beginning of the stream. In this way, data may be transferred from the module to the module.

Next, a second example of packing in data transfer will be described with reference to FIG. 20. In the first example described above, only the shift processing is performed on the transferred data, and the data size is not changed. On the other hand, data streams are often limited in resources. For this reason, it may be necessary to reduce the size of data to be transferred and reduce the amount of information to be transferred.

Figure 20:
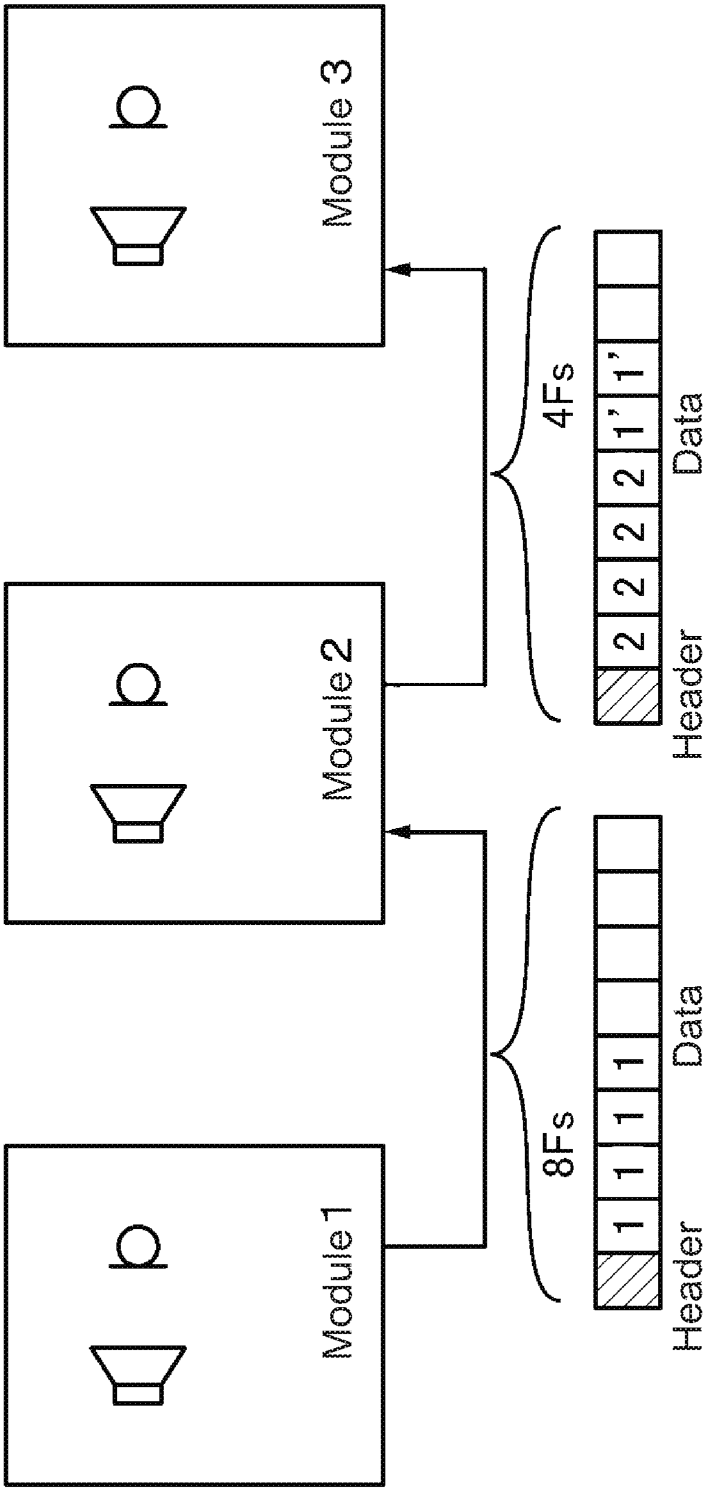
FIG. 20 A diagram illustrating a second example of packing in data transfer.

Therefore, as shown in FIG. 20, the data size is reduced and the transfer is performed. Data is transferred from the module 1 to the module 2. In addition, data is transferred from the module 2 to the module 3. When data is transferred from the module 1 to the module 2, the module 2 first pulls up the transmitted data. Next, when the acquired data is an audio signal, the data size is reduced. The data size is reduced by lowering the sampling frequency, lowering the bit rate, or the like. Next, right shift is performed on the data with reduced data size. In this way, resources are allocated so that the data owned by the module 2 itself may be inserted. Then, the data of the module 2 itself is inserted at the beginning of the stream. In this way, the data size is reduced to ensure resources. In addition, data may be transferred from the module to the module.

Incidentally, the data "1" in FIG. 20 represents 16-bit data of the module 1, the data "1'" represents 8-bit data of the module 1.

Figure 21:
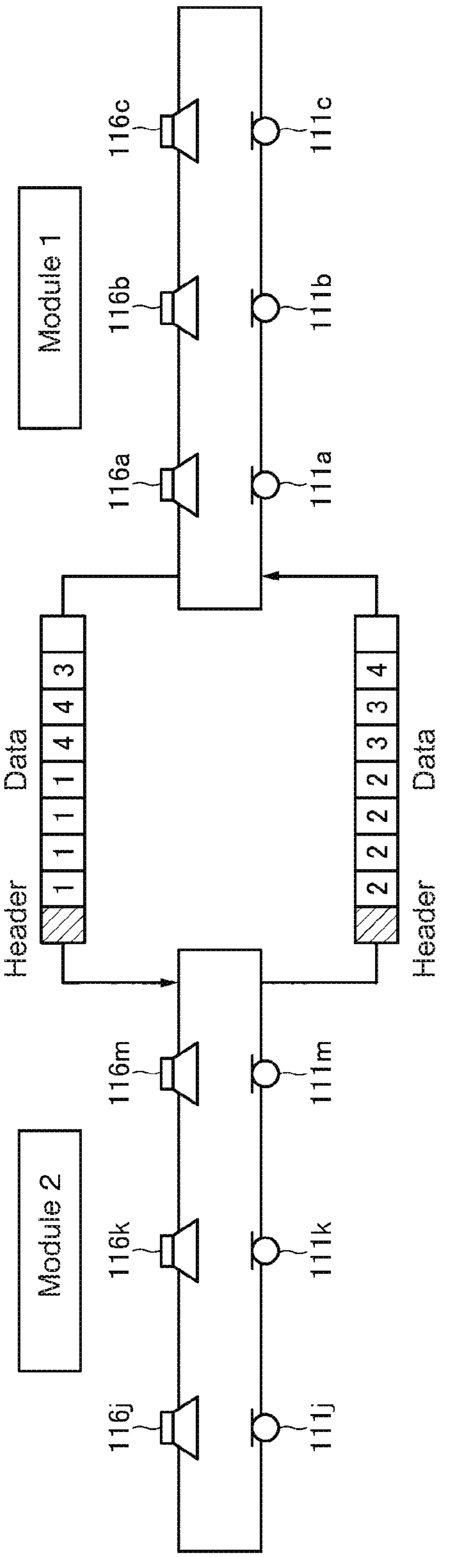
FIG. 21 A diagram illustrating a data transfer in the module configuration shown in FIG. 18.

Next, data transfer between modules when the modules 1 to 4 are configured as shown in FIG. 18 will be described with reference to FIG. 21. In the configuration shown in FIG. 18, the module 1 and the module 2 are adjacent to each other. It may be seen that the contribution ratio is high in forming a 3-input and 3-output system. In FIG. 21, numerical values assigned to data indicate data in each module. Data transferred from the module 1 to the module 2 includes data in the module 1, data in the module 4, and data in the module 3.

Therefore, it is assumed that the dedicated bus has bidirectional communication during data transfer. In the data transfer from the module 1 to the module 2, the audio signal collected by the reference microphone in the module 1 has the highest importance. On the other hand, in data transfer from the module 2 to the module 1, the audio signal collected by the reference microphone in the module 2 has the highest importance.

Therefore, as shown in FIG. 21, the data is transferred from the module 1 to the module 2 in such a manner that the data size of the audio signal collected by the microphone connected to the module 1 becomes the largest. On the other hand, data is transferred from the module 2 to the module 1 in such a manner that the data size of the audio signal collected by the module 2 becomes the largest. In FIG. 21, the data transferred from the module 1 to the module 2 includes the data of the modules 3 and 4 that have already been transferred to the module 1. The module 1 is transferred to the module 2 with the largest data size. The data transferred from the module 2 to the module 1 includes the data of the modules 3 and 4 that have already been transferred to the module 2. The data of the module 2 is transferred to the module 1 with the largest size.

Figure 22:
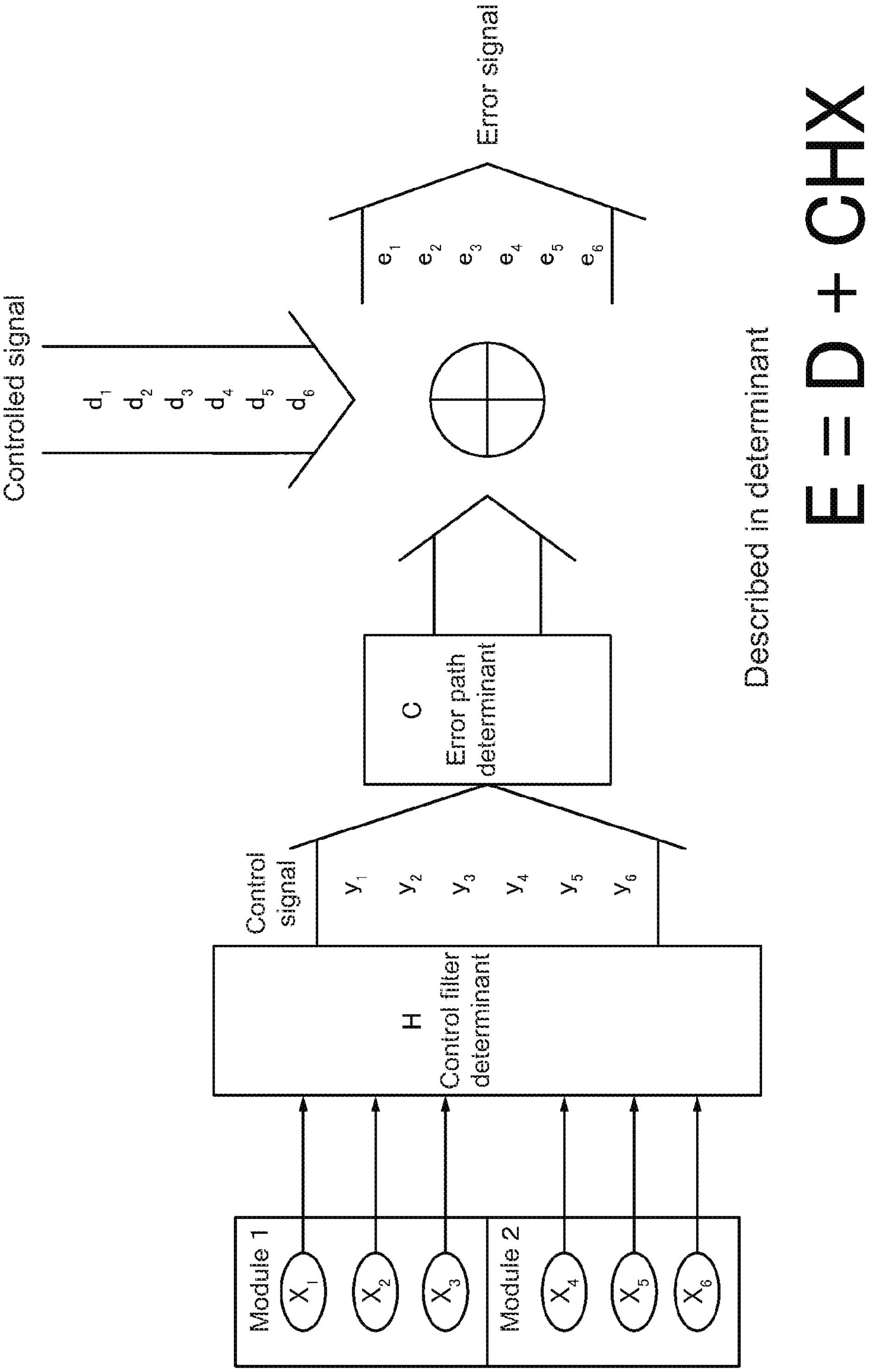
FIG. 22 A diagram illustrating an example of performing a multi-input and multi-output process by using the reference signal collected by the reference microphone of the two adjacent modules.

FIG. 22 is a block diagram illustrating processing when performing multi-input and multi-output processing using audio signals (hereinafter, referred to as reference signals) collected by reference microphones of two adjacent modules. FIG. 22 generally illustrates noise canceling of the feedforward system in a determinant.

Figure 23:
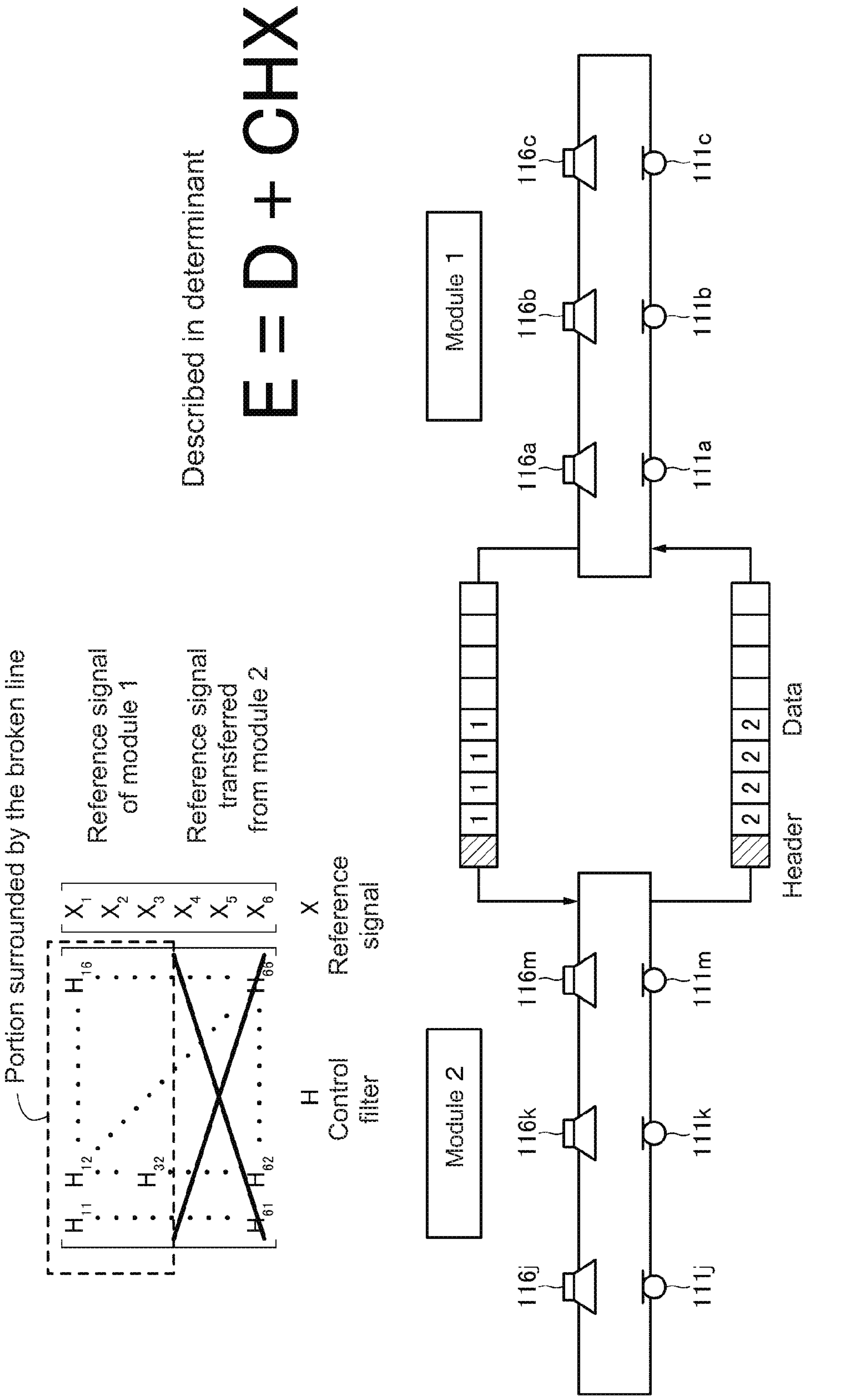
FIG. 23 A diagram illustrating an example of performing a multi-input and multi-output process by using the reference signal collected by the reference microphone of the two adjacent modules.

Here, in the module 1 and the module 2 shown in FIG. 18, the reference signal collected by the microphone connected to the module 2 is transferred to the module 1, and the reference signal is used in the module 1. In this case, it will be described what signal processing is possible in the module 1. FIG. 23 shows a determinant in the module 1. The module 1 may use the audio signal collected by the reference microphone of the module 1 and the audio signal collected by the reference microphone of the module 2 as the reference signal. Therefore, the calculation amount corresponding to the portion surrounded by the broken line of the control filter H in FIG. 23 may be assigned to the module 1. The module 2 is similar.

Figure 24:
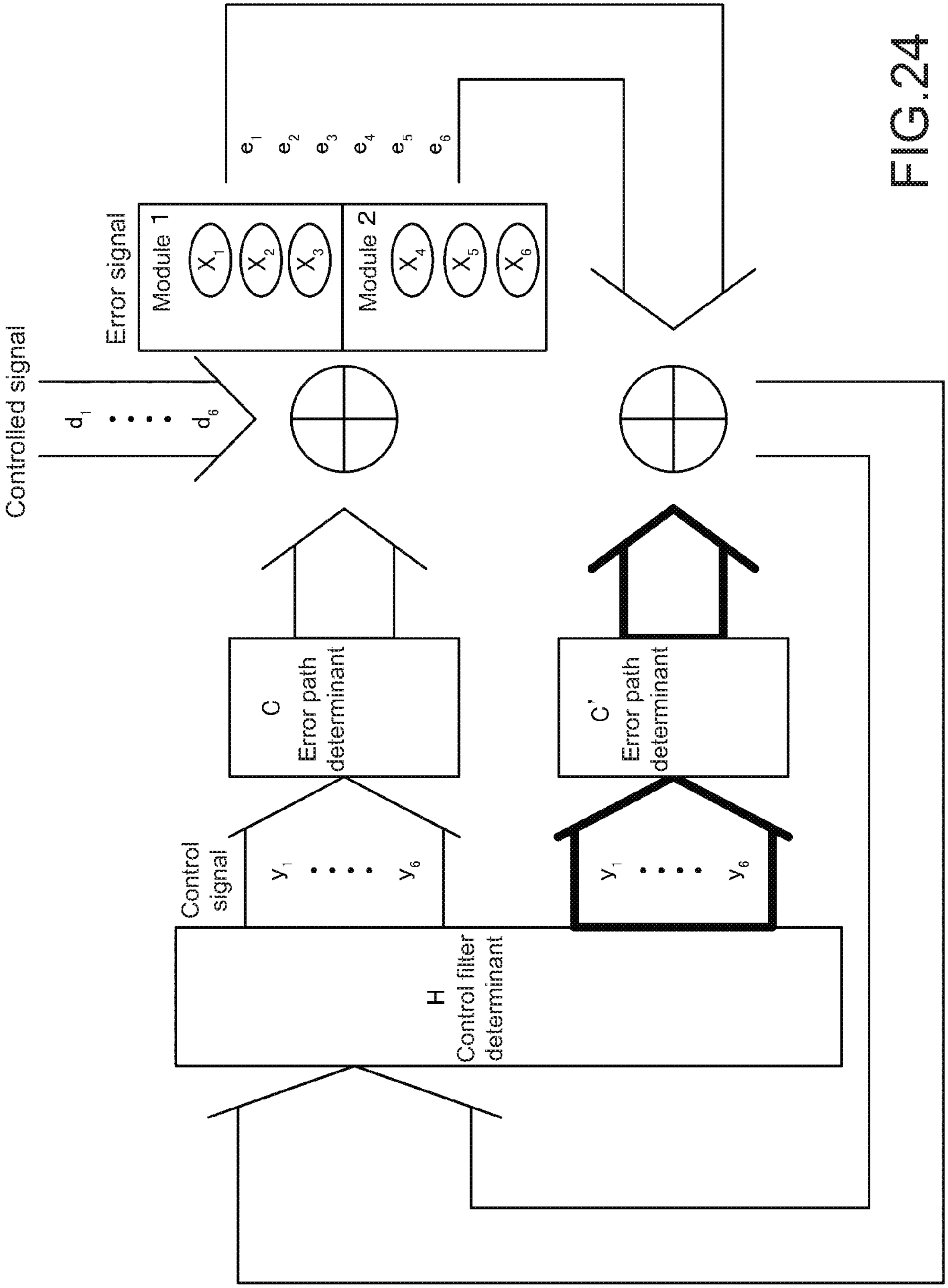
FIG. 24 A signal processing block diagram in a second feedback system in a multi-input and multi-output system.

FIG. 24 shows a signal processing block diagram in a second feedback system in a multi-input and multi-output system. The basic configuration is the same processing as that shown in FIG. 21. In the second feedback system in the multi-input and multi-output system, the output signal indicated by the thick line also needs to be transferred in the same manner as the error signal.

The signal processing apparatus according to the present technology is configured as described above. According to the present technology, it is possible to easily expand the scale of the signal processing system performing noise canceling by daisy-chain connection. For example, as the multi-input and multi-output processing, it is possible to perform the feedforward noise canceling processing of the multi-input and multi-output and the feedback process of the multi-input and multi-output.

In addition, a multi-input and multi-output system may be controlled by communication using a dedicated bus. This makes it possible to use modules suitable for the control scale. For example, a system that uses both a feedforward system and a feedback system is implemented, and in addition, two feedback systems are used together. It is possible to adopt such an algorithm with high noise reduction performance.

Control information between connected signal processing apparatuses may be managed by communication using a dedicated bus. A suitable filter for noise cancellation may be selected. Noise canceling may be turned on or off.

Further, the signal processing system is constructed in a circular form. Thus, it is possible to effectively reduce the noise arriving from the outside to the inside by processing in a multi-stage manner. Or it is possible to effectively reduce the noise arriving from the inside to the outside by processing in a multistage manner. When the signal processing system is configured in a circular shape, data is transferred in accordance with the importance level. Thus, the audio signal collected by the microphone in the outer circle is used as an error microphone for the outer speaker. The audio signal is used as a reference microphone for the inner speaker. Thus, it is possible to improve the noise canceling performance.

2. Modifications

The embodiments of the present technology have been described above in detail, but the present technology is not limited to the above-described embodiments, and various modifications based on the technical idea of the present technology are possible.

The connection of the plurality of signal processing apparatuses 100 is not limited to the dedicated bus 150. If the effect of the present technology may be achieved, the plurality of signal processing apparatuses 100 may be connected by a general-purpose bus. Further, connection of a plurality of signal processing apparatuses 100 is not limited to daisy-chain connection. The plurality of signal processing apparatuses 100 may be connected in other connection forms as long as the effects of the present technology may be achieved. Other connection forms include, for example, star, ring, etc.

The present technology may also be configured as follows.

(1) A signal processing apparatus, including:

a noise canceling processing unit connectable to one or a plurality of input units and connectable to one or a plurality of output units, a plurality of the signal processing apparatuses being connected one another and configured to execute noise canceling processing.

(2) The signal processing apparatus according to the item (1), in which the plurality of signal processing apparatuses are daisy-chain connected.

(3) The signal processing apparatus according to the item (1) or (2), in which a plurality of the noise canceling processing units transfer data therebetween.

(4) The signal processing apparatus according to the item (3), in which the data is an audio signal input from the one or plurality of input units.

(5) The signal processing apparatus according to the item (3) or (4), in which the data is a cancellation signal output from the one or plurality of output units.

(6) The signal processing apparatus according to the item (3) or (4), in which the data is control information.

(7) The information processing apparatus according to any one of the items (3) to (6), in which a size of the data is reduced and the data is transferred.

(8) The information processing apparatus according to the item (7), in which the size of the data is reduced by lowering a sampling frequency.

(9) The information processing apparatus according to the item (7) or (8), in which the size of the data is reduced by lowering a bit rate.

(10) The signal processing apparatus according to any one of the items (1) to (9), in which one of a plurality of the noise canceling processing units, to which the input unit close to a noise source is connected, transfers the data to another one of the plurality of noise canceling processing units, to which the input unit far from the noise source is connected.

(11) The signal processing apparatus according to any one of the items (1) to (10), in which the signal processing apparatus is connected to a noise analyzer unit that analyzes a noise, and switches the noise canceling processing depending on an analysis result of the noise analyzer unit.

(12) The signal processing apparatus according to the item (11), in which the signal processing apparatus switches a mode of the noise canceling processing depending on the analysis result of the noise analyzer unit.

(13) The signal processing apparatus according to the item (11) or (12), in which the noise canceling processing unit is capable of executing the noise canceling processing of a plurality of systems, and changes a combination of the systems depending on the analysis result of the noise analyzer unit.

(14) The signal processing apparatus according to any one of the items (1) to (13), in which the plurality of input units and the plurality of output units are connected to any of a plurality of the noise canceling processing units connected one another.

(15) A signal processing method, including:

connecting a plurality of signal processing apparatuses one another and executing noise canceling processing, each of the plurality of signal processing apparatuses including a noise canceling processing unit connectable to one or a plurality of input units and connectable to one or a plurality of output units.

(16) A signal processing program that causes a computer to execute a signal processing method including connecting a plurality of signal processing apparatuses one another and executing noise canceling processing, each of the plurality of signal processing apparatuses including a noise canceling processing unit connectable to one or a plurality of input units and connectable to one or a plurality of output units.

REFERENCE SIGNS LIST

100 signal processing apparatus
101 noise canceling processing unit
111 microphone
116 speaker

The invention claimed is:

1. A first signal processing apparatus, comprising:
- a first noise canceling processing unit connectable to:
  - a first input unit of a plurality of input units, and
  - at least one output unit of a plurality of output units, wherein
  - the first signal processing apparatus is connected to a second signal processing apparatus of a plurality of signal processing apparatuses,
  - the plurality of signal processing apparatuses includes the first signal processing apparatus,
  - the second signal processing apparatus includes a second noise canceling processing unit connected to a second input unit of the plurality of input units,
  - the first input unit is closer to a noise source than the second input unit, and
  - the first noise canceling processing unit is configured to:
    - execute a noise canceling process; and
    - transfer data to the second noise canceling processing unit.

2. The first signal processing apparatus according to claim 1, wherein signal processing apparatuses of the plurality of signal processing apparatuses are daisy-chain connected.

3. The first signal processing apparatus according to claim 1, wherein the data is an audio signal input from the first input unit.

4. The first signal processing apparatus according to claim 1, wherein the data is a cancellation signal output from the at least one output unit.

5. The first signal processing apparatus according to claim 1, wherein the data is control information.

6. The first signal processing apparatus according to claim 1, wherein the first signal processing apparatus is configured to:
- reduce a size of the data; and
- control the transfer of the data based on the reduction of the size of the data.

7. The first signal processing apparatus according to claim 6, wherein the first signal processing apparatus is further configured to lower a sampling frequency of the data to reduce the size of the data.

8. The first signal processing apparatus according to claim 6, wherein the first signal processing apparatus is further configured to lower a bit rate of the data to reduce the size of the data.

9. The first signal processing apparatus according to claim 1, wherein
- the first signal processing apparatus is connected to a noise analyzer unit,
- the noise analyzer unit:
  - analyzes a noise to obtain an analysis result, and
  - transmit the analysis result to the first signal processing apparatus, and
- the first signal processing apparatus is further configured to switch the noise canceling process based on the analysis result of the noise analyzer unit.

10. The first signal processing apparatus according to claim 9, wherein the first signal processing apparatus is further configured to switch a mode of the noise canceling process based on the analysis result of the noise analyzer unit.

11. The first signal processing apparatus according to claim 9, wherein the noise canceling processing unit is further configured to:
- execute the noise canceling process for a plurality of systems; and change a combination of the plurality of systems based on the analysis result of the noise analyzer unit.

12. The first signal processing apparatus according to claim 1, wherein each signal processing apparatus of the plurality of the signal processing apparatuses is connected to a respective noise canceling processing unit of a plurality of noise canceling processing units, the plurality of noise canceling processing units includes the first noise canceling processing unit and the second noise canceling processing unit, and the plurality of input units and the plurality of output units are connected to at least one of the plurality of the noise canceling processing units.

13. A signal processing method, comprising:

executing, by a first noise canceling processing unit of a first signal processing apparatus, a noise canceling process, wherein the first noise canceling processing unit is connectable to:

a first input unit of a plurality of input units, and at least one output unit of a plurality of output units, the first signal processing apparatus is connected to a second signal processing apparatus of a plurality of signal processing apparatuses, the plurality of signal processing apparatuses includes the first signal processing apparatus, the second signal processing apparatus includes a second noise canceling processing unit, the second noise canceling processing unit is connected to a second input unit of the plurality of input units, and the first input unit is closer to a noise source than the second input unit; and transferring, by the first noise canceling processing unit, data to the second noise canceling processing unit.

14. A non-transitory computer-readable medium having stored thereon computer-executable instructions, which when executed by a processor, cause the processor to execute operations, the operations comprising:

executing, by a first noise canceling processing unit of a first signal processing apparatus, a noise canceling process, wherein the first noise canceling processing unit is connectable to:

a first input unit of a plurality of input units, and at least one output unit of a plurality of output units;

the first signal processing apparatus is connected to a second signal processing apparatus of a plurality of signal processing apparatuses, the plurality of signal processing apparatuses includes the first signal processing apparatus, the second signal processing apparatus includes a second noise canceling processing unit, the second noise canceling processing unit is connected to a second input unit of the plurality of input units, and the first input unit is closer to a noise source than the second input unit; and transferring, by the first noise canceling processing unit, data to the second noise canceling processing unit.

* * * * *